(12) United States Patent
Romesberg, III et al.

(10) Patent No.: US 7,519,150 B2
(45) Date of Patent: Apr. 14, 2009

(54) SYSTEM FOR ENHANCING INTENSITY MODULATED RADIATION THERAPY, PROGRAM PRODUCT, AND RELATED METHODS

(75) Inventors: Merle E. Romesberg, III, Pittsburgh, PA (US); Paul S. Nizin, Sugar Land, TX (US); Ramiro Pino, Pearland, TX (US)

(73) Assignee: Best Medical International, Inc., Springfield, VA (US)

( * ) Notice: Subject to any disclaimer, the term of this patent is extended or adjusted under 35 U.S.C. 154(b) by 0 days.

(21) Appl. No.: 11/828,979

(22) Filed: Jul. 26, 2007

(65) Prior Publication Data

US 2008/0049898 A1 Feb. 28, 2008

Related U.S. Application Data

(60) Provisional application No. 60/833,653, filed on Jul. 26, 2006.

(51) Int. Cl.
*A61N 5/10* (2006.01)

(52) U.S. Cl. .......................................... 378/65; 378/64

(58) Field of Classification Search ................... 378/64, 378/65
See application file for complete search history.

(56) References Cited

U.S. PATENT DOCUMENTS

| | | | |
|---|---|---|---|
| 2005/0111621 A1 | 5/2005 | Riker et al. | |
| 2006/0285640 A1 | 12/2006 | Nizin et al. | |

OTHER PUBLICATIONS

Papanikolaou, "Tissue Inhomogeneity Corrections for Megavoltage Photon Beams"; Aug. 2004, AAPM Report No. 85; American Assoc. Of Physicists in Medicine by Medical Physics Publishing.
NOMOS Radiation Oncology; "CORVUS Inverse Treatment Planning, CORVUS Beam Utilities User Manual"; Aug. 2006 Rev. 1; P/N 209361; NOMOS Radiation Oncology.
M. Romesberg, et al., "A Novel, Heterogeneity Inclusive, Pencil Beam Based Algorithm to Improve Lung IMRT Using the CORVUS Planning System", abstract Jun. 2006.
CORVUS Inverse Treatment Planning, CORVUS Beam Utilities User's Manual, North America Scientific, NOMOS Radiation Oncology Division, A Division of North American Scientific, Rev. 1, 270 pp. (2006).

(Continued)

*Primary Examiner*—Jurie Yun
(74) *Attorney, Agent, or Firm*—Bracewell & Giuliani LLP

(57) ABSTRACT

A system to provide enhanced computational efficiency in determining dose in a media of varying density from a high-energy radiation-beam for radiation treatment, program product, and related methods are provided. The system can include a radiation treatment planning computer and radiation treatment planning program product adapted to enhance optimization of a radiation treatment plan for delivering radiation to a complex medium defining a patient volume. The program product provides functions including those for predetermining a delivery machine-dependent representation of radiation dose for different electron densities selected over a representative range, predetermining a depth-dependent representation of central axis properties of a pencil beam passing through a complex medium, and determining with constant time computational complexity, radiation dose for each of a plurality of points of interest in a heterogeneous medium having a complex spatial distribution of heterogeneous electron densities by applying the predetermined machine-dependent and depth-dependent representations.

56 Claims, 17 Drawing Sheets

OTHER PUBLICATIONS

CORVUS Inverse Treatment Planning, CORVUS User's Manual, North America Scientific, NOMOS Radiation Oncology Division, A Division of North American Scientific, Rev. 1, 511 pp. (2006).

M. Romesberg, "Real Time Isodose Sculpting, CDVH Manipulation, and Delivery Efficiency Control in IMRT,"AAPM Meeting (2005).

R. Pino, "A Heterogeneity Inclusive FSPB Algorithm," Dept. of Radiology, Baylor College of Medicine, and The Methodist Hospital, Houston TX (2004).

R. Pino, "Central -Axis Depth-Dose Curves for Inhomogeneous Medium With Arbitrary Variations of the Density," Department of Radiology, Baylor College of Medicine, and The Methodist Hospital, Houston, TX (2005).

M. Romesberg, et al.,"SU-DD-A1-05; Real-Time Isodose Sculpting, CDVH Manipulation and Delivery Efficiency Control in IMRT," Med. Phys. 32, p. 1896 (2005), AAPM Meeting.

A. Van Esch, "Testing of the Analytical Anisotropic Algorithm for Photon Dose Calculation," Med. Phys. 33, 4130 (2006).

M. Romesberg, et al., "A Novel, Heterogeneity Inclusive, Pencil Beam Based Algorithm to Improve Lung IMRT Using the CORVUS Planning System", presented at the American Association of Physicists in Medicine, Aug. 3, 2006.

Complex IMRT (Isodose)

PEREGRINE® Monte Carlo

| | Dose (%) | Dose (Gy) |
|---|---|---|
| ——— | 10.0 | 6.82 |
| — — — | 20.0 | 13.64 |
| – – – – | 30.0 | 20.47 |
| - - - - - | 40.0 | 27.29 |
| ·········· | 50.0 | 34.11 |
| ——— | 60.0 | 40.93 |
| — — — | 70.0 | 47.76 |
| — — — — | 80.0 | 54.58 |
| — — — — — | 90.0 | 61.40 |
| ············ | 95.3 | 65.02 |

New Model
(w Real-time Stochastic Estimation)

⦿ CTV  ○ PTV
Total Accumulated Dose

| Target Name | Goal(Gy) | Min(Gy) | Max(Gy) | Mean(Gy) |
|---|---|---|---|---|
| Target1 | 65.00 | 54.23 | 70.87 | 64.32 |
| Target2 | 55.00 | 45.88 | 68.65 | 59.37 |

| Structure Name | Limit(Gy) | Min(Gy) | Max(Gy) | Mean(Gy) |
|---|---|---|---|---|
| Tissue | 55.00 | | | |
| Non-target Tissue | 55.00 | | 64.93 | 16.53 |
| Esophagus | 45.00 | 0.40 | 61.00 | 16.53 |
| Heart | 45.00 | 0.39 | 1.30 | 0.67 |
| Lung (L) | 30.00 | 0.38 | 58.74 | 8.44 |
| Lung (R) | 30.00 | 0.11 | 46.37 | 4.79 |
| Ref1 ( ) | 45.00 | | 53.93 | 6.99 |

PEREGRINE® Monte Carlo

⦿ CTV  ○ PTV
Total Accumulated Dose

| Target Name | Goal(Gy) | Min(Gy) | Max(Gy) | Mean(Gy) |
|---|---|---|---|---|
| Target1 | 65.00 | 54.92 | 68.22 | 63.39 |
| Target2 | 55.00 | 46.08 | 67.88 | 50.48 |

| Structure Name | Limit(Gy) | Min(Gy) | Max(Gy) | Mean(Gy) |
|---|---|---|---|---|
| Tissue | 55.00 | | 68.22 | 3.48 |
| Non-target Tissue | 55.00 | | 64.13 | 3.32 |
| Esophagus | 45.00 | | 62.42 | 16.74 |
| Heart | 45.00 | 0.34 | 1.36 | 0.69 |
| Lung (L) | 30.00 | 0.34 | 58.67 | 8.90 |
| Lung (R) | 30.00 | 0.34 | 44.35 | 5.26 |
| Ref1 ( ) | 45.00 | | 54.24 | 7.53 |

RMS difference of Min and Max doses between New Model and PEREGRINE® = 2%

Fig. 21

SYSTEM FOR ENHANCING INTENSITY MODULATED RADIATION THERAPY, PROGRAM PRODUCT, AND RELATED METHODS

RELATED APPLICATIONS

This non-provisional application claims priority to and the benefit of U.S. Patent Application No. 60/833,653 filed on Jul. 26, 2006, titled "System for Enhancing Intensity Modulated Radiation Therapy, Program Product, and Related Methods," incorporated herein by reference in its entirety.

BACKGROUND OF THE INVENTION

1. Field of The Invention

The present invention relates generally to radiation therapy. More specifically, the present invention relates to a system, program product, and related methods for determining radiation dose to be delivered according to a radiation treatment plan.

2. Description of the Related Art

Radiation therapy can be effective in treating certain types of cancerous tumors, lesions, or other "targets." A vast majority of such targets can be eradicated completely if a sufficient radiation dose is delivered to the tumor or lesion volume. High-energy radiation is absorbed and scattered by matter. Cancer cells forming the tumors are often more sensitive to radiation than normal cells, so radiation treatment is often used to fight cancerous tumors. Those tumors are usually deep inside the body, and when radiation coming from an external source is applied, it is inevitable that normal surrounding tissue will receive radiation. The objective is thus to give the tumor a lethal amount of radiation while keeping under acceptable levels the amount of radiation that healthy tissue will receive. For most of the cases high energy photons and electrons are employed for treatment, but protons, neutrons, heavy charged particles, etc, are also used. Complications, however, may result from use of the necessary effective radiation dose due to damage to healthy tissue which surrounds the target or to other healthy body organs located close to the target. The goal of the various radiation procedures, such as conformal radiation therapy treatment, nevertheless, is to confine the delivered radiation dose to only the target volume defined by the outer surfaces of the target, while minimizing the dose of radiation to surrounding healthy tissue or adjacent healthy organs. If the effective radiation dose is not delivered to the proper location within the patient, serious complications may result.

Radiation treatment therapy delivery typically uses a radiation delivery apparatus, such as, for example, a linear accelerator or other radiation producing source, to treat the target. The conventional linear accelerator includes a rotating gantry which generally rotates about a horizontal axis and which has a radiation beam source positionable about the patient which can direct a radiation beam toward the target to be treated. The linear accelerator can also include a rotating treatment table which generally rotates about a vertical axis and which can position the target within a rotational plane of the rotating gantry. Various types of devices or apparatus can set the field size to further conform the shape of the radiation treatment beam during rotation of the radiation beam source to follow the spatial contour of the target, as viewed with respect to the radiation treatment beam, as it passes through the patient's body into the target. The modern radiation sources, such as the linear accelerator, have primary collimators (jaws) that set the field size. Often they are also equipped with special collimators, e.g., multi-leaf collimators (MLC), which have multiple leaf or finger projections that can be programmed to move individually into and out of the path of the radiation beam to shape the radiation beam to dynamically shape the field of irradiation in order to deliver dose in the desired way.

Typically, the patient has the radiation therapy treatment plan prepared based upon a diagnostic study utilizing computerized tomographic ("CT") scanning, magnetic resonance ("MR") imaging, or conventional simulation films which are plain x-rays generated with the patient. This radiation therapy treatment plan is developed such that the patient's tumor or lesion is in the position that will be used during the radiation therapy treatment. Various types of radiation treatment planning systems can be used to create the radiation treatment plan which, when implemented, will deliver a specified dose of radiation shaped to conform to the target volume, while limiting the radiation dose delivered to sensitive surrounding healthy tissue or adjacent healthy organs or structures. Various forms of radiation treatment planning include forward planning and inverse planning. In forward planning the physicist directly controls the machine settings of the beams by manually setting the shape and radiation dose of each field utilizing knowledge of a past treatments in order to achieve expectations of the physician. With inverse planning the physician directly prescribes the desired target dose and tolerances for sensitive structures, and the optimization software determines machine settings that will most closely deliver the prescribed radiation distribution. In the case of both forward planning and inverse planning, a procedure is required to calculate the radiation dose associated with the machine settings of the beam. In inverse planning, the optimization software explores a multitude of possibilities for the beam settings so that computational complexity (calculation time) is critical. To this end, the radiation beam field can be partitioned into many small rectangular or square shaped fields which are generically called finite-size pencil beams (FSPB) or pencil beams, for short. That is, a large radiation beam field can be composed of many pencil beams. The FSPBs allow for optimal partitioning of the radiation field and they are computationally efficient for calculating dose distributions of complex modulated fields. In the intensity modulated radiation therapy (IMRT), once the parameters for the pencil beams are computed, their intensities are modulated until the optimal dose distribution is achieved. From a computational point of view, FSPB dose values can be stored in tables and a table lookup method can be used.

Most current methods used to calculate the dose delivered to the target volume and surrounding structure are based on dose measurements made in a water box. Heterogeneities such as bone and airways are treated in an approximate way or otherwise ignored altogether. Next to direct measurements, the most accurate way of calculating dose in a heterogeneous medium is employing the Monte Carlo (MC) method. Superposition/convolution is a close alternative. Hundreds or even thousands of pencil beams need to be pre-computed for a regular treatment plan. Traditional Monte Carlo and superposition/convolution algorithms require computing the dose distribution for entire volume in order to determine dose a single point of interest. Thus, both algorithms are computationally very expensive. Monte Carlo requires simulating tens of millions of particles through the whole volume to calculate radiation dose at the point of interest. Superposition/convolution requires completion of a 3D convolution to calculate radiation dose at a point of interest. Due to the enormous amount of point dose calculations required to optimize a plan, use of the Monte Carlo method, without modification, will remain impractical for inverse planning.

A. Van Esch, et al, in an article titled "Testing Of The Analytical Anisotropic Algorithm For Photon Dose Calculation," Med. Phys. 33, 4130 (2006), describes an algorithm known as the Varian AAA inhomogeneity algorithm, which calculates "photon dose . . . as a three-dimensional convolution of Monte-Carlo precalculated scatter kernels, . . . ." Cormen et al. in, e.g., "Introduction to Algorithms", The MIT Press, Cambridge Mass. (1997), however, indicates that a convolution, most efficiently implemented through the Fast Fourier transform, is known to have computational complexity O(n lg n), where "n" is the size of the vector being convolved and 'lg' represents a logarithm with undisclosed base. An alternative method of computing primary central axis dose is based upon convolution with a forward and backward spread function rather than a finite difference equation, described, e.g., in a publication titled "A Method Of Calculating High-Energy Photon Primary Absorbed Dose In Water Using Forward And Backward Spread Dose-Distribution Functions," Med. Phys. 12, 731 (1985), again, is a non-constant time operation.

Monte-Carlo codes such as PEREGRINE®, described, e.g., in C. Hartmann, et al, "Description and Dosimetric Verification of the PEREGRINE® Monte Carlo Dose Calculation System for Photon Beams Incident on a Water Phantom," Med. Phys. 28, 1322 (2001), require a full simulation to determine dose at a single point, and thus, cannot determine dose to a single point in constant time. Likewise, even a fast variant of superposition convolution, such as, for example, the Collapsed Cone method, described, e.g., by A. Ahnesjo, in a publication titled "Collapsed Cone Convolution of Radiant Energy for Photon Dose Calculation in Heterogeneous Media," Med. Phys. 16, 577 (1989), require a full simulation to determine dose at a single point. Similarly, direct application of a Clarkson Integration for inhomogeneous media, sector integration is required for each point of interest; integration also being a non-constant time operation.

Accordingly, neither the Monte Carlo nor superposition/convolution methods can compute dose to a point with constant time computational complexity. Rather, computing dose to a single point requires simulation of the energy transport through the entire spatial distribution of electron densities. As a result, computing dose to a small subset of points in a volume essentially requires calculating dose to the whole volume. IMRT optimization requires rapid exploration of a multitude of candidate treatment plan solutions to some points of interest. Full simulation cannot be employed for each of the multitude of candidates. Interactive manipulation of radiation dose distributions as in U.S. Patent Application 20050111621 requires rapid calculation of a few high-resolution dose images which are beyond the capabilities of the transport simulating algorithms.

The traditional pencil-beam method was developed to provide dose computations to a point with constant time computational complexity. This method, however, has significant inaccuracies in regions of lateral disequilibrium such as for a narrow beam passing through the lung or other region of electron density below that of water as in Nizin, "Electronic Equilibrium and Primary Dose in Collimated Photon Beams," Med. Phys. 20, p. 258 (1982). Lateral disequilibrium is an effect of electron scattering: when the beam is small or energy is high in low-density media, such as lung material, the traditional model will systematically overestimate the central axis dose and underestimate the width of the beam. This method also has significant inaccuracies in media having lateral heterogeneities whereby the beam experiences a variation in electron density across the beam front at a given depth. These inaccuracies typically separately result in an overestimate of central axis dose in the lower electron density portion. Further, this method has significant inaccuracies in media having a complex electron density distribution such as the human body because it does not adequately account for multiple build-up and build-down regions characteristic of media having a complex electron density distribution. Rather, this method employs a single dose build-up restriction provided to model initial dose entry into the media. For complex media, such restriction typically results in an overestimate of central axis dose in points or regions having an electron density other than that of water, particularly with respect to narrow or high-energy beam fields.

There have been efforts to improve the results for when the traditional pencil-beam method is used in heterogeneous media. Many such efforts, however, assumed the beam was passing through a slab geometry phantom where the electron densities did not vary in a fully three-dimensional manner. For example, one traditional method of accounting for heterogeneities called the effective path length method (EPL) amounts to substituting the integral of electron densities along a path for the depth. Such attempts to improve the traditional pencil beam method, however, only account for part of the effect of the heterogeneous media through an effective path length by adding up the electron densities at all the points between the skin and the depth of interest. Specifically, these attempts to improve the traditional pencil-beam method do not address the important effects of penumbra widening in the lung or other low density structure and the effects of lateral heterogeneities as the radiation beam passes through the complex electron density distribution of the human body. Nor do they address the effects of the complex electron distribution resulting in continuous density changes, and thus, continuous build-up/build-down.

A few research avenues are noted regarding Monte Carlo inverse planning which relate to the use of pencil beam algorithms. First, Monte Carlo can be employed in conjunction with a pencil-beam algorithm. In such case, Monte Carlo calculations are preformed on a few iterations using pencil-beam calculations in intermediate iterations as described in Siebers, et al, in "Performance of a hybrid MC dose algorithm for IMRT optimization dose evaluation," Med. Phys. 34, 2853 (2007). Recognized by the Applicants is that numerous calculations would still be required to obtain dose at a single point of interest, and that improvements to the pencil-beam accuracy would be desirable. Second, Monte Carlo generated pencil-beams can be applied as described in Bergman et al., in "Direct Aperture Optimization for IMRT Using Monte Carlo Generated Beamlets," Med. Phys. 33, 3666 (2006). Recognized by the Applicants is that the points of interest used for optimization must be pre-selected rather than arbitrarily placed, that calculating dose at a point of interest that was not preselected would require a complete Monte Carlo simulation, and that this avenue does not provide a system or a method of updating an arbitrary 2d image profiles in real-time. Accordingly, recognized by the Applicants is the need for a system and method which can generalize the Monte Carlo generated central axis data to off-axis profiles calculation, for example, to enable interactive 2d dose image calculations.

Regardless of which methodology is used at the time of a diagnostic study to develop the radiation therapy treatment plan, in the delivery of either conformal radiation therapy treatments or static radiation therapy treatments, an accurate and repeatable determination of radiation dose to the delivered is very important. Successful radiation therapy depends on accurately placing the proper amount of radiation upon the target without unnecessarily damaging surrounding tissue.

Thus, it is necessary to relate the radiation dose determined to be delivered to the target at the time of the diagnostic study to the radiation dose actually delivered at the time of the radiation therapy treatment. If the actual dose is not correct, the result can be under-treating the target tumor or lesion and/or damaging healthy surrounding tissue and organs.

Recognized, therefore, by the Applicants is the need for a system, program product, and methods for determining and determining dose to be delivered to a patient that provides enhanced accuracy for real-time dose optimization, provides values at three-dimensional point without needing to determine values for the entire volume or subset thereof, that accounts for reduced actual dose and wider penumbra resulting from lateral electronic disequilibrium, that accounts for the complex electron density distribution of the human body, and that accounts for variations in electron density across the beam front or lateral heterogeneities, to thereby provide enhanced accuracy for determining dose in low-density, e.g., lung, material particularly when using narrow or high beam energy.

SUMMARY OF THE INVENTION

In view of the foregoing, embodiments of the present invention provide a solution which is both cost efficient and time efficient and which includes a system, program product, and method for determining dose to be delivered to a patient that provides enhanced accuracy for real-time dose optimization, provides values at three-dimensional point without needing to determine values for the entire volume or subset thereof, that accounts for reduced central axis dose and wider penumbra resulting from lateral electronic disequilibrium, that accounts for dose build-up and build-down due to the complex electron density distribution of the human body, and that accounts for variations in electron density across the beam front or lateral heterogeneities, to thereby provide enhanced accuracy for determining dose delivered to a patient.

Embodiments of the present invention provide electron density-dependent parameterization of a new finite size pencil beam (FSPB) model. Embodiments of the present invention also provide a process for determining field and medium dependent normalization factors for primary dose which include electron disequilibrium, a process for determining central axis (CAX) primary dose for each FSPB and storage for future table look-up during dose calculation, a process for determining and storing primary profiles for homogeneous media, for several electron densities, using density-dependent lateral build-up coefficient and kernel integration, a process for determining and storing scatter profiles for homogeneous media several densities using Clarkson integration with density-rescaled field sizes, a process for determining profiles by looking up profiles corresponding to the local electron density, and a process for determining profiles near interfaces by making a linear combination of the current and previous profiles. Embodiments of the present invention also provide a combination of all the above processes in order to produce a finite-size pencil beam for dose calculation in forward and inverse planning.

More specifically, embodiments of the present invention include a system for determining dose in heterogeneous media of varying electron density from, for example, a therapeutic high-energy radiation-beam for radiation treatment. The system can include an image gathering device, e.g., CT scanner, accessible to a communication network to provide an at least two-dimensional image slice of a tumor target volume and an adjacent structure volume in a patient, a radiation beam source to deliver radiation to the tumor target according to a radiation treatment plan, and a radiation treatment planning computer in communication with the image gathering device and having memory, a processor coupled to the memory. Note, the radiation treatment planning computer can function as a stand-alone computer or as a networked device, as described above.

The system can include radiation treatment planning program product stored, for example, in the memory of the radiation treatment planning computer and adapted to produce an optimized radiation treatment plan for delivering radiation to the tumor target volume simulated dose calculation program product. The radiation treatment planning program product can include instructions that, when executed by the radiation treatment planning computer, can perform the operations of receiving a set of photon beam data for a water medium, e.g., water tank, to thereby parameterize a dose model for unit electron density, and parameterizing a machine-dependent dose model for unit electron density responsive to the set of photon beam data. The parameterization process can include dividing a dose model into primary and scatter dose.

The operations can also include determining a machine-dependent primary dose profile for each of a first set of a plurality of electron densities distributed through a preselected range of electron densities responsive to the dose model for unit electron density, and determining a machine-dependent scatter dose profile for each of a second set of a plurality of electron densities distributed through a preselected range of electron densities responsive to the dose model for unit electron density. This data can be saved in look-up tables for ready reference and determining density dependent values.

The operations can also include determining patient specific primary dose profile parameters for each of the plurality of pencil beams to be utilized during radiation treatment responsive to the primary dose profiles, and determining patient specific scatter dose profile parameters for each of the plurality of pencil beam to be utilized during radiation treatment. These parameters allow for patient specific modeling of each FSPB to be used for a radiation treatment plan to allow for running multiple beam-intensity scenarios to determine optimum beam intensity for each individual FSPB.

The operations can also include retrieving the patient specific primary and scatter dose profile parameters separately for each of a plurality of points of interest in a patient volume to compute dose with constant time computational complexity to each point of interest responsive to a local electron density value for the respective point of interest to thereby determine total dose at each of the plurality of points of interest, and producing a map of radiation dose delivered to the patient volume to allow a user to iteratively evaluate the total dose of the patient volume. The local electron density value can be a single value of electron density associated with the respective point of interest or an electron density distribution associated the respective point of interest.

Embodiments the present invention also include methods of determining dose in a media of varying electron density from a high-energy radiation-beam for radiation treatment. For example, an embodiment of a method can include the steps of predetermining a delivery machine-dependent representation of radiation dose for a plurality of different electron densities selected over a preselected representative range, predetermining a depth-dependent representation of central axis properties of a pencil beam passing through a complex medium having a complex spatial distribution of heterogeneous electron densities for each of a plurality of pencil beams, and determining with constant time computational complexity radiation dose for each of a plurality of points of interest in the complex medium by applying the predetermined machine-dependent and depth-dependent representations.

The step of predetermining a delivery machine-dependent representation of radiation dose can include the steps of receiving data parameters for a medium having properties, for example, substantially similar to that of water, forming a primary dose profile table for each of the plurality of electron densities responsive to the data parameters, and forming a scatter dose profile table for at least a representative portion of the plurality of electron densities. The step of predetermining a depth dependent representation of central axis properties of a pencil beam passing through a complex medium for each of a plurality of pencil beams can include the steps of receiving electron density parameters for a patient volume developed from a patient-specific image generating device, determining current and previous electron density values for each of a plurality of depths along each separate one of a plurality of pencil beams, determining a separate depth dependent weight for each of the plurality of depths, and determining a depth-dependent effective electron density for each of the plurality of depths to thereby form at least one table of off-axis dose parameters including representations of a plurality of regions of dose build-up and dose build-down. The step of determining with constant time computational complexity radiation dose for each of a plurality of points of interest in the complex medium can include the steps of determining for each of a plurality of points of interest a local density value, and retrieving the stored off-axis dose parameters responsive to the local electron density value for each of the plurality of points of interest.

Embodiments the present invention also include methods of determining central axis dose in a media of varying electron density from a high-energy radiation-beam for radiation treatment. For example, the method can include the step of modeling a dose profile by performing the step of determining a difference between a current central axis dose and a central axis dose at previous depth traveling into a complex medium along a central axis of a pencil beam in proportion to a product of a difference between the central axis dose at previous depth and an equilibrium dose to a homogeneous medium having an electron density at a point of interest, and an electron density dependent proportionality constant that depends on the electron density at the point of interest, and determining the sum of the central axis dose at previous depth and the difference between the current central axis dose and the central axis dose at previous depth, to thereby form representations of a plurality of regions of dose build-up and dose build-down. The electron density-dependent proportionality constant can depend, e.g., linearly, on a ratio of electron density of the medium and an associated proportionality constant applied to a medium having properties substantially similar to that of water.

Embodiments the present invention also include methods of determining an off-axis dose profile in heterogeneous media of varying electron density from a therapeutic high-energy radiation beam for radiation treatment. For example, the method can include the steps of receiving a central axis primary dose, receiving homogeneous medium off-axis primary dose profiles for a plurality of electron densities, and determining an off-axis primary dose profile for a region of a complex medium having an electron density varying with depth along a central axis of a pencil beam by forming a combination of homogeneous medium off-axis primary dose profiles equal the central axis primary dose, e.g., by forming a combination of homogeneous medium off-axis primary dose profiles weighted by values applied so that penumbra implies central axis dose in agreement with that computed via a differential equation substantially centered about the central axis. The method can also include receiving a central axis scatter dose, receiving homogeneous medium off-axis scatter dose profiles for a plurality of densities, and determining an off-axis scatter dose profile for a region of a complex medium having an electron density varying with depth along a central axis of a pencil beam from off-axis properties of a homogeneous medium corresponding to an effective electron density selected so that central axis scatter dose of the determined homogeneous medium off-axis profile matches the received central axis scatter dose of the complex medium.

Embodiments the present invention also include methods of determining dose in heterogeneous media of varying density from a therapeutic high-energy radiation-beam for radiation treatment. For example, the method can include the step of determining an off-axis dose profile for a pencil beam to a point of interest of a complex medium having an electron density distribution varying laterally at a depth of interest associated with the point of interest by using an off-axis dose profile of the pencil beam at a depth and an off-axis position of interest corresponding to the electron density distribution substantially equal to that of a local electron density distribution near the point of interest.

According to another embodiment of the method, the method can include the step of determining for a preselected size pencil beam, a central axis primary dose in a homogeneous medium of arbitrary electron density from a central axis primary dose model for water equivalent medium of an equivalent effective field size by rescaling a dose normalization factor and a linear attenuation and longitudinal buildup coefficients as a function of the arbitrary electron density. The method can also or alternatively include receiving a central axis scatter dose model representing central axis scatter dose as a function of field size and depth for water equivalent medium, determining a central axis scatter dose model representing central axis scatter dose as a function of field size and depth for a homogeneous medium of arbitrary electron density using an equivalent effective field size responsive to the received scatter dose model, and determining at least one scatter volume for a homogeneous medium of arbitrary electron density by performing a modified Clarkson integration utilizing the determined central axis scatter dose model of the homogeneous medium of arbitrary electron density in the integration to derive the scatter volume.

Embodiments the present invention also include a computer readable medium including instructions that when executed by a computer such as, for example, the radiation treatment planning computer, can perform the necessary steps to develop a model for determining dose in a media of varying electron density from a high-energy radiation-beam for radiation treatment. For example, an embodiment of a computer readable medium can include instructions to perform the operations of predetermining a delivery machine-dependent representation of radiation dose for a plurality of different electron densities selected over a preselected representative range, predetermining for each of a plurality of pencil beams a depth-dependent representation of central axis properties of a pencil beam passing through a complex medium having a complex spatial distribution of heterogeneous electron densities, and determining with constant time computational complexity radiation dose for each of a plurality of points of interest in the complex medium by applying the predetermined machine-dependent and depth-dependent representations.

The operation of predetermining a delivery machine-dependent representation of radiation dose can include the operations of determining an at least two-dimensional primary dose profile for each of the plurality of different electron densities and an at least two-dimensional scatter dose profile for at least a representative portion of the plurality of different electron densities.

The operation of predetermining a depth dependent representation of central axis properties of a pencil beam passing through a complex medium for each of a plurality of pencil beams can include the operation of determining a depth-dependent weighted value to form a weight for a primary dose profile for a point at a current electron density at a current depth and a weight for at least one dose profile for a corresponding at least one point at a previous electron density at a previous depth so that when the weighted values are applied to a linear combination of the dose profiles a resulting dose profile provides a value substantially equal to a convoluted value of central axis primary dose at the current depth when a point of interest applied to the linear combination at the current depth is on the central axis. It can also include the operation of determining an effective electron density to apply to a scatter dose profile that when applied provides a value substantially equal to a convoluted value of central axis scatter dose at the current depth when a point of interest applied to the scatter dose profile at the current electron density at the current depth is on the central axis.

The operation of determining with constant time computational complexity radiation dose for each of a plurality of points of interest in a complex medium can include the operations of determining for each of a plurality of points of interest a local electron density value, and accessing or retrieving predetermined off-axis properties corresponding to a homogeneous density having a value derived from the respective local electron density value associated with each point of interest responsive to the respective local electron density value for each respective one of the plurality of points of interest and a pencil beam intensity for each associated pencil beam directed through each respective one of the plurality of points of interest to thereby determine radiation dose for each of the plurality of points of interest.

An embodiment of the computer readable medium can include instructions to perform the operation of modeling a dose profile by performing the step of determining a differential change to central axis dose traveling into a complex medium along a central axis of a pencil beam in proportion to a product of a difference between a current central axis dose and a dose to homogeneous medium having an electron density at a point of interest and an electron density dependent proportionality constant that depends on the electron density at the point of interest to thereby form representations of a plurality of regions of dose build-up and dose build-down.

An embodiment of the computer readable medium can include instructions to perform the operations of receiving a central axis primary dose, receiving homogeneous medium off-axis primary dose profiles for a plurality of electron densities, and determining an off-axis primary dose profile for a region of a complex medium having an electron density varying with depth along a central axis of a pencil beam by forming a linear combination of the homogeneous medium dose profiles weighted by values applied so that penumbra implies a central axis dose agreeing with central axis dose computed via a differential equation, e.g., the center of the determined off-axis primary dose profile has primary dose substantially equal to the perceived central axis primary dose. The operations, can also or alternatively include the steps of receiving a central axis scatter dose, receiving homogeneous medium off-axis scatter dose profiles for a plurality of densities, determining an off-axis scatter dose profile for a region of a complex medium having an electron density varying with depth along a central axis of a pencil beam from off axis properties of a homogeneous medium having an effective electron density selected so that central axis scatter dose in the determined homogeneous medium off-axis profile substantially matches the received central axis scatter dose of the complex medium.

An embodiment of the computer readable medium can include instructions to perform the operation of determining an off-axis dose profile for a pencil beam to a point of interest of a complex medium having an electron density distribution varying laterally at a depth of interest associated with the point of interest by using an off-axis dose profile of the pencil beam at the depth of interest corresponding to the electron density distribution substantially equal to that of a local electron density distribution near the point of interest.

An embodiment of the computer readable medium can include instructions to perform the operations of determining for a preselected size pencil beam, a central axis primary dose in a homogeneous medium of arbitrary electron density from a central axis primary dose model for water equivalent medium of an equivalent effective field size by rescaling a dose normalization factor and a linear attenuation and longitudinal buildup coefficients as a function of the arbitrary electron density; and determining for a preselected size pencil beam, a central axis scatter dose in a homogeneous medium from a central axis scatter dose model for water equivalent medium of an equivalent effective field size by using density-scaled scatter dose values.

Advantageously, embodiments of the present invention preserve the pencil beam model due to its computational efficiency, but at the same time, generalize it in such a way that it can effectively deal with electronic disequilibrium in circumstances where the electron density varies from voxel to voxel, from point to point, in a grid of step of a few millimeters, e.g., typically 1-5 mm. To minimize the number of additional computations necessary to account for electronic disequilibrium, embodiments of the present invention provide for storing a plurality of arrays corresponding to the CAX primary dose of each FSPB and various profiles, which can be retrieved and employed to determine primary and/or total dose at each point of interest for evaluating dose.

Advantageously, according to an embodiment of the present invention, to utilize the enhanced FSPB model, a set of photon beam data in water can be acquired in order to parameterize the model for unit density. Separation of scatter and primary dose in water can be performed similar to that done in the traditional model. For the central axis primary and scatter dose, a set of equations can be solved and the results stored for each pencil beam involved in the radiation treatment plan. Profiles can be calculated and stored for a set of electron densities and then retrieved depending on the local electron density of the point of interest or a nearby point or distribution of points. Each FSPB can then be composed and superimposed with other FSPBs in order to evaluate the dose at the point of interest. Further, due to physical and mathematical similarities, the method and model can also be advantageously applied to the calculation of neutron dose in heterogeneous media along with other forms of energy.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIGS. 20A-24 are schematic and graphic illustrations illustrating the agreement between the new model and Monte Carlo.

DETAILED DESCRIPTION

The present invention will now be described more fully hereinafter with reference to the accompanying drawings, which illustrate embodiments of the invention. The present invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
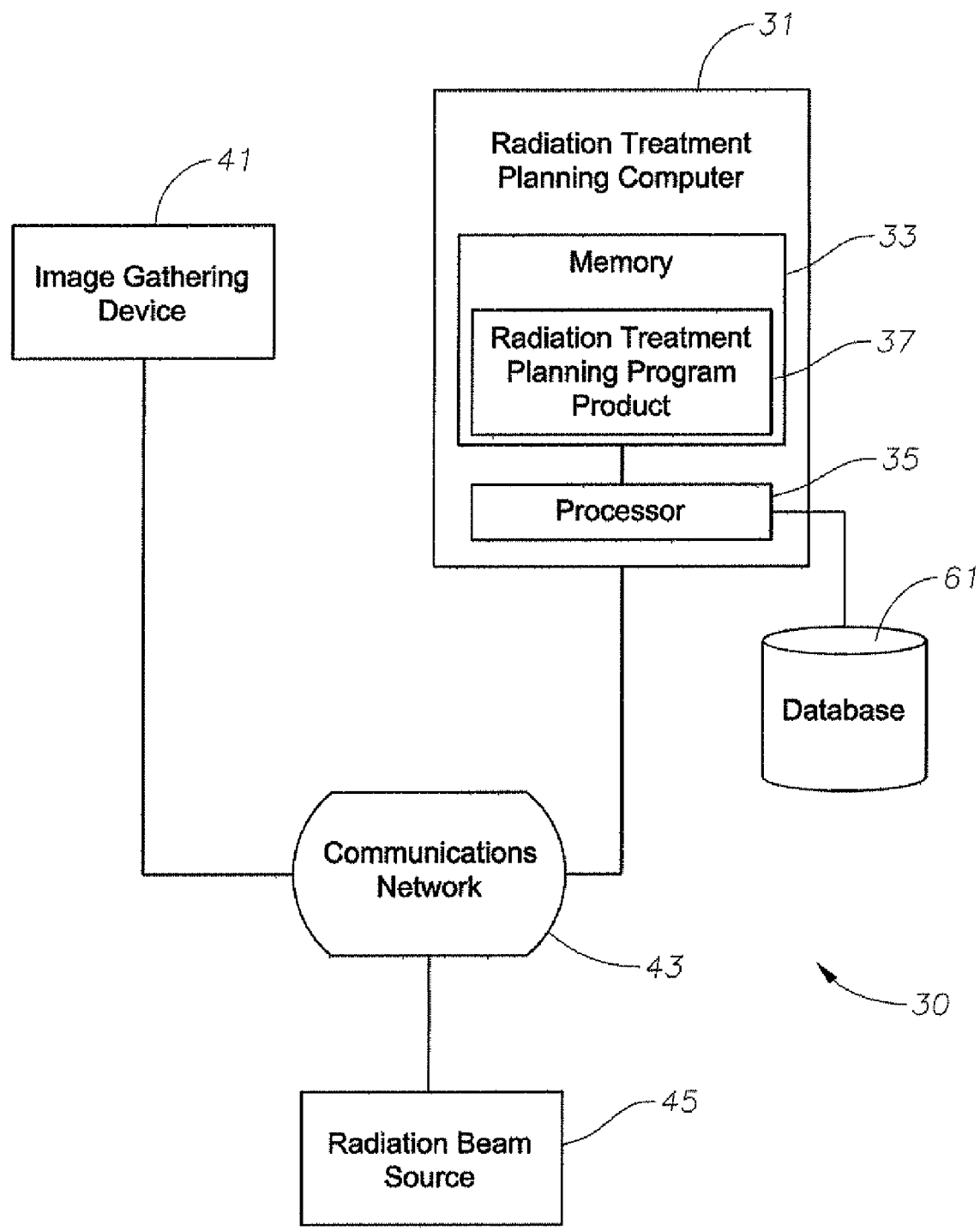
FIG. 1 is a schematic diagram of a system to determine dose in heterogeneous media of varying density from a therapeutic high-energy radiation-beam for radiation treatment according to an embodiment of the present invention.

As shown in FIGS. 1-25, embodiments of the present invention include systems and methods for determining dose in heterogeneous media of varying density from a therapeutic high-energy radiation-beam for radiation treatment. For example, as shown in FIG. 1, a system 30 can include a radiation treatment planning computer 31 having memory 33, a processor 35 in communication with the memory 33, and radiation treatment planning program product 37 stored at least partially in the memory 33 and adapted to produce an optimized radiation treatment plan for delivering radiation to the tumor target volume. The system also includes an image gathering device 41, e.g., computed tomography (CT) scanner or other imaging device known to those skilled in the art, accessible to a communication network 43 to provide stacks of two-dimensional image slices or a three-dimensional image of a tumor target volume and an adjacent structure volume in a patient or phantom used to develop the treatment plan. The system 30 further includes a radiation beam source 45, e.g., linear accelerator or other delivery device known to those skilled in the art, to deliver radiation to the tumor target according to the radiation treatment plan. The radiation can be in the form of photons, neutrons, electrons, protons, or other particles. According to the exemplary embodiment of the present invention, the following description will concentrate mostly on high-energy photon beams, which can originate in man-made sources such as the linear accelerator as x-rays or can be generated in the nucleus of certain elements such as Cobalt-60 as gamma rays.

According to an embodiment of the system 30, the memory 33 can include volatile and nonvolatile memory known to those skilled in the art including, for example, RAM, ROM, and magnetic or optical disks, just to name a few. The radiation treatment planning program product 37 can be a stand-alone product or an add-on module or other software or program product element forming a portion of a larger treatment planning system such as, for example, the Corvus treatment planning system available through Nomos Corporation, Cranberry Township, Pa., assignee of the present invention, or others known to those skilled in the art. The program product 37 can be in the form of microcode, programs, routines, and symbolic languages that provide a specific set or sets of ordered operations that control the functioning of the hardware and direct its operation, as known and understood by those skilled in the art. Similarly, the radiation treatment planning computer 31, image gathering device 41, and radiation beam source 45, or combination thereof, can be embodied in a single apparatus within the same housing or in separate housings.

Embodiments of the present invention also include methods employed by the system 30 which includes pre-, during-, and post-radiation treatment planning steps for operations that implement the use of fields partitioned into many small, normally rectangular or square shaped fields, which are generically referred to as finite-size pencil beams (FSPB) or pencil beams, for short, which can be readily modeled in the form of cylinders having a given radius. FSPBs can allow for optimal partitioning of the radiation field and they are computationally efficient for calculating dose distributions of complex modulated fields. FSPBs have some significant fundamental advantages. For example, FSPBs can be used to calculate dose to any single point (as specified a posteriori) much more rapidly than an entire patient volume (not true for Monte Carlo or superposition/convolution). This can be critical for intensity modulated radiation therapy (IMRT), as they can enable real-time dose manipulation, where thousands of pencil beams may need to be pre-computed for a regular treatment plan. That is, once the parameters for the pencil beams are computed, their intensities can be iteratively modulated, determining each point of interest at a constant time computational complexity, until the optimal dose distribution is achieved. See glossary, table 1 at para. [00103] for various terminology used herein. See also reference publications, table 2 at para. [00104] each incorporated by reference in its entirety.

An advantage of constant time complexity per point of interest is that if the dose at any spot or point is desired after changing a pencil-beam intensity in the optimization loop, the "answer" in compute time can be obtained on the order of a table lookup (O(1)). By contrast, if a fall 3d convolution is required, each time a pencil-beam intensity changes, one would need to wait a much more significant amount of time to obtain an entire 3D volume to derive that one result. In computer science, 'big O' notation referring to the asymptotic upper bound, is frequently used to compare the performance of various algorithms without regard to specific implementation (Cormen et al., p. 26). Convolution, as most efficiently implemented using the fast fourier transform, has computational complexity O(n lg n) where "n" is the size of the vectors being convolved and 'lg' represents a logarithm with undisclosed base. Full 3d convolution, as applied to calculate dose for a Cartesian grid with N element on each side (having a total of $N^3$ elements) for a single divergent beam of radiation, has computational complexity $O(N^3 \lg N)$ (Ahnesjo "Collapsed Cone", p. 587). Various methods are known to improve this bound for the purpose of computing the entire 3D dose volume. The method according to an embodiment of the present invention, however, is significantly differentiated over that of the prior methodologies by beneficially providing dose to a single point from a single pencil-beam in O(1) time (without a priori knowledge regarding the location of the single point). Importantly, this can be employed to quickly update dose in the optimization loop and also to quickly compute dose to specific 2d planes of calculation without requiring an entire 3d calculation.

From a computational point of view, the FSPB value calculation parameters and/or dose values for each pencil beam can be stored in one or more tables and a table lookup method can be used to enhance computational efficiency. Pencil beams also have other advantages including the implementation of dose shaping and histogram manipulation techniques that allow for quick and user controlled interactive changes in treatment plans that may further improve their quality.

Figure 2:
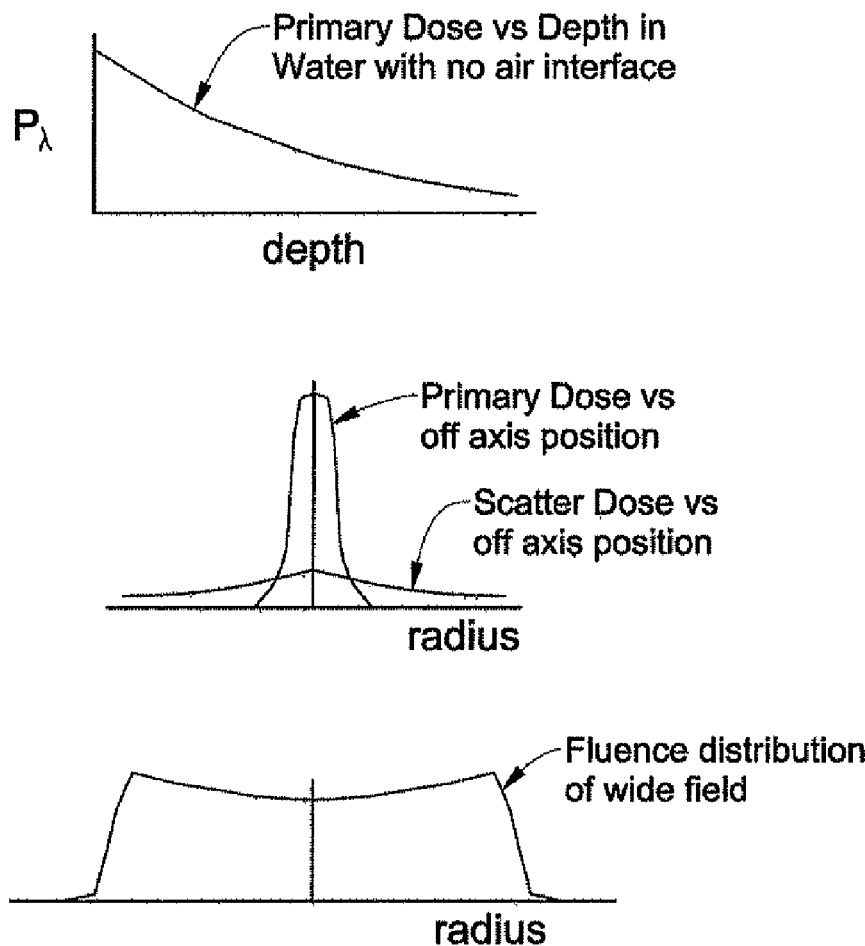
FIG. 2 is a schematic diagram illustrating the qualitative behavior of CAX primary dose in homogenous material without any interface, primary dose profile, scatter dose and primary fluence.
Figure 3:
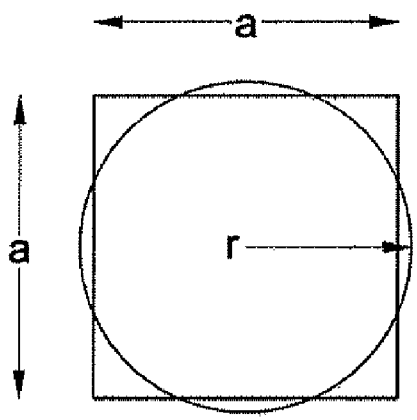
FIG. 3 is a schematic diagram illustrating modeling of a square pencil beam of width a using an equivalent radius (r)

The FSPB data table can include central axis (CAX) equilibrium primary dose, primary dose profile, scatter dose, and the primary fluence profile. Primary dose is the amount of energy per unit mass deposited in matter as a result of the first interaction of a photon, scatter dose is the amount of dose deposited due to scattered photons, and primary fluence is the number of photons per unit area incident in the material. FIG. 2 illustrates the qualitative behavior of CAX primary dose, primary dose profile, scatter dose and primary fluence.

Dose at a point of interest i in an FSPB for water-like medium can be determined using various methodologies known to those skilled in the art. According to one particular methodology, for example, the dose at point i in an FSPB of equivalent radius r is calculated using the following expression:

$$D_i(R,d) = ISC \cdot F(R) \cdot [P_\lambda(d) \cdot E(r) \cdot N(R,d) + S(R,d)],$$

where ISC is the inverse square correction factor that accounts for beam divergence. The depth of i in the FSPB (d) and off-axis distance (R) are used to retrieve the CAX primary dose, primary profile, scatter and primary fluence as in Nizin "Phenomenological Dose Model for Therapeutic Photon Beams: Basic Concepts and Definitions," Med. Phys. 26, p. 1893 (1999). The term $P_\lambda(d)$ in this example represents equilibrium primary dose which includes dose build-up only at the interface between air and the patient skin (or the phantom) and a corresponding exponential decay of photon fluence, and can be determined using the following expression:

$$P_\lambda(d) = P_0[1-\exp(-\beta d)]\exp(-\mu d),$$

where $P_0$ is a normalization factor, $\mu$ is the linear attenuation coefficient, and $\beta$ is the longitudinal build-up coefficient for water. The equilibrium factor E(r), describing radiological penumbra, is field-size dependent due to electronic transport and should reflect electronic disequilibrium. According to this example, it is modeled using the following expression:

$$E(r) = 1 - \exp(-\gamma r),$$

where $\gamma$ is the lateral build-up coefficient and r is the effective radius of the beam.

In this example, the equivalent radius is r=0.561a where a is the side width of a square pencil beam. As perhaps best shown in FIG. 3, an equivalent radius r can be used to model a square or rectangular pencil beam.

An objective of the optimization procedure can include obtaining a set of transmission factors to form a transmission map that optimizes the dose distribution giving a set of constraints. The total dose in a generic beam can be calculated as a superposition of pencil beams weighted by the intensity (transmission) factors Ti as:

$$D(r,d)=\Sigma_i T_i D_i.$$

The properties of the radiation beam depend on the photon energy, characteristics of the machine, and the medium where radiation is absorbed. Regularly, measurements are performed in water for each machine, since some of the parameters of the model will be machine dependent. Absorbed dose in the central axis can be measured for a series of beam sizes and a primary-scatter dose separation can be performed using, for example, the z=rd/(r+d) function whereby d is depth and r is the beam radius as in Björngard, et al, in "Description of the Scatter Component in Photon-Beams," Med. Phys. 33, 21 (1988). Further profile measurements can be taken and from there, FSPB parameters can be determined. According to one model ("Corvus 6.3, Beam Utilities User's Manual", p. A1-A38), dose can be separated as:

$$D(d,r)=P_\lambda(d)+S(d,r),$$

where r represents the radius of a circular field having equivalent central axis properties as in Björngard, et al, in "A Note on Equivalent Circles, Squares, and Rectangles," Med. Phys. 9, 258 (1982).

According to another model form, dose can be separated as:

$$D(x,y,d)=P(x,y,d)+S(x,y,d).$$

Regardless of the modeling form, from the primary dose, the linear attenuation coefficient μ and the longitudinal build-up coefficient β can be extracted. Similarly, the value of the lateral build-up coefficient γ can be calculated using an analytical relationship between μ and γ. The scatter data can be stored in the form of, for example, three-dimensional tables.

Due to radiation transport and source and collimator design, profiles are not perfectly sharp, i.e., they are not step-like, but there is a penumbra. Primary radiation penumbra is usually separated into geometric penumbra and radiological penumbra. Geometric penumbra is caused by the finite size of the photon source and the presence and characteristics of the collimators. Radiological penumbra is caused by radiation transport. Geometric penumbra can be modeled using Gaussian functions, while radiological penumbra can be described by the function exp(−γ·r)/r.

The total primary dose profile is the convolution of geometric and radiological penumbra, and the physical aperture of the beamlet (Rect), and can be modeled using the following expression:

$$N(x,y)=Rect(x/w,y/h)Geometric(x,y)Radiological(r),$$

where ** stands for the operation of convolution and r=(x²+y²)^(1/2). If we convolve the aperture with the geometric penumbra we obtain $P_G$ geometric penumbra component. Substituting the elements in the convolution, the above equation will look as follows:

$$P(u,v) = N(x,y)$$

$$= \gamma N \int_{-\infty}^{+\infty} dx \int_{-\infty}^{+\infty} dy \frac{\exp(-\gamma\sqrt{x^2+y^2})}{\sqrt{x^2+y^2}} P_G(x-u; w; \sigma_x) P_G(y-v; h; \sigma_y),$$

where N is a normalization factor, $P_G$ is a geometric penumbra component; w and h are the dimensions of the (rectangular) pencil beam; and $\sigma_x$ and $\sigma_y$ are the geometric penumbra coefficients, and where:

$$P_G(x; w; \sigma_x) = \frac{1}{\sigma_x}\left[\text{erf}\left(\frac{x+w/2}{\sigma_x}\right) - \text{erf}\left(\frac{x-w/2}{\sigma_x}\right)\right],$$

which can be evaluated numerically, for example, using Fast Fourier Transforms.

Figure 4:
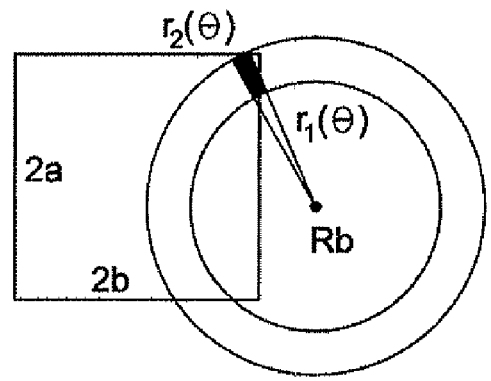
FIG. 4 is a schematic diagram illustrating the calculation of scatter dose for a point outside a radiation beamlet.

Scatter profiles can be calculated using, for example, Clarkson (sector) integration as described for water in "Corvus 6.3, User's Manual", p A1-A38. FIG. 4 illustrates the calculation of scatter dose for a point outside the beamlet (Rb) illustrated as a 2a by 2b rectangle, using the equation:

$$S(Rb) = \frac{1}{2\pi}\int_0^{2\pi} d\theta[S_C(r_2(\theta)) - S_C(r_1(\theta))],$$

where $S_C(r)$ is the CAX scatter dose for a beam of radius r at a given depth d.

For a point inside the beamlet (2a by 2b rectangle) the equation is similar, just there is no $S_C(R_1(\theta))$, i.e.:

$$S(Rb) = \frac{1}{2\pi}\int_0^{2\pi} d\theta S_C(r_2(\theta)).$$

The equation for CAX scatter dose can be written in a more general form as:

$$S(x,y,d) = \frac{1}{2\pi}\int_0^{2\pi} S(r(\theta), d) d\theta.$$

The model described above is generally adequate for homogeneous water-like systems, but complex media such as, for example, the human body is made of muscle; fat which are more or less water equivalent; bone which is about two times more dense than water; lung which is of a variable density, approximately four times less than that of water; and other tissue, etc. Thus, in order to obtain an accurate dose calculation, heterogeneity corrections need to be included. Traditional FSPB models, however, include only radiological path-length corrections, which amount to calculating an effective depth that includes variations of the density. The effective depth (or effective path length (EPL)) can be described by the following equation:

$$d_{\mathit{eff}}(d) = \int_0^d \rho e(l) dl,$$

where $\rho_e$ is the electron density having unit value for water and where d represents the depth of interest.

Once calculated, the effective depth $d_{\mathit{eff}}$ can be used to evaluate central axis dose at the effective depth by substituting d with $d_{\mathit{eff}}$. According to this model, total dose can be described by the following equation:

$$D(x,y,d)=P(x,y,d_{\mathit{eff}}(d))+S(x,y,d_{\mathit{eff}}(d)),$$

where:
P(x,y,d)=P(d,r).N(x,y), which models primary dose,
$P(d,r)=P_0(1-\exp(-\beta d))\exp(-\mu d)$, which models in a single build-up/build-down, and
N(x,y)=Rect(x/w,y/h)Radiological(r)Geometric(r), which models the penumbra, where Radiological(r)=$(\gamma/2\pi)*\exp(-\gamma r)/r$, and where both Radiological(r) and Geometric(r) integrate to unity.

It has been documented that these corrections are insufficient, particularly for low density regions such as the lung. The reason is that this correction neglects a phenomenon called electronic disequilibrium which arises when more radiation is scattered away from the region of interest than the one incoming from adjacent regions. Discrepancies between measured and calculated dose values using radiological pathlength corrections can be quite large, especially for small fields/higher energies. To account for the electronic disequilibrium, embodiments of the present invention preserve the pencil beam model due to its computational efficiency, but at the same time, generalize it in such a way that it can effectively deal with electronic disequilibrium in circumstances where the density varies from voxel to voxel, from point to point, in a grid of step of a few millimeters, e.g., typically 1-5 mm. Particularly, embodiments of the system 30 and methods account for reduced actual dose and wider penumbra resulting from lateral electronic disequilibrium, account for dose build-up and dose build-down due to the complex electron density distribution of the human body, and lateral heterogeneities or account for variations in electron density across the beam front, to thereby provide enhanced accuracy for determining dose delivered to a patient.

Figure 5:
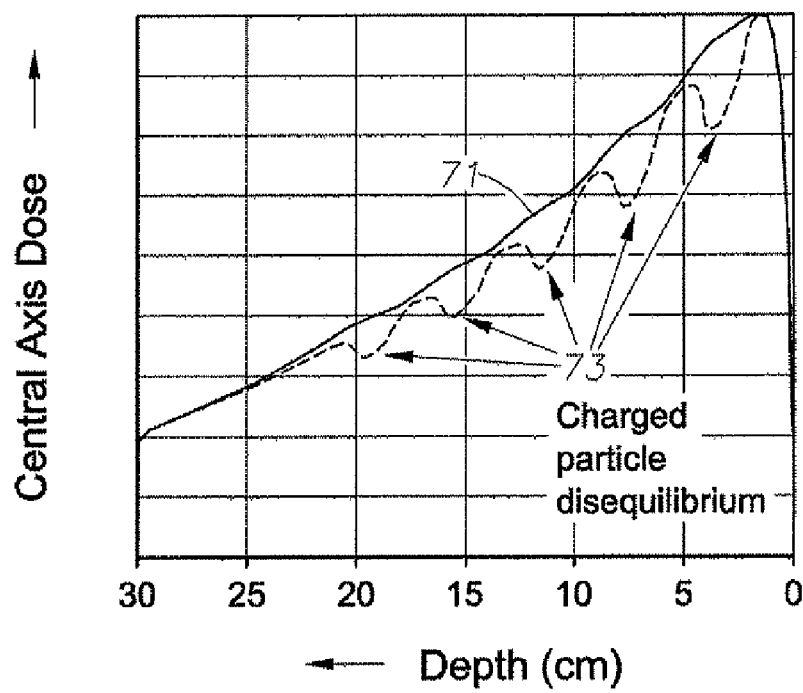
FIGS. 5 and 6 are graph diagrams illustrating a comparison between calculated dose using the traditional pencil beam model and a calculated dose provided by a Monte Carlo simulation for a 3×3 cm filed in a phantom having alternating 2 cm layers of water and lung.
Figure 6:
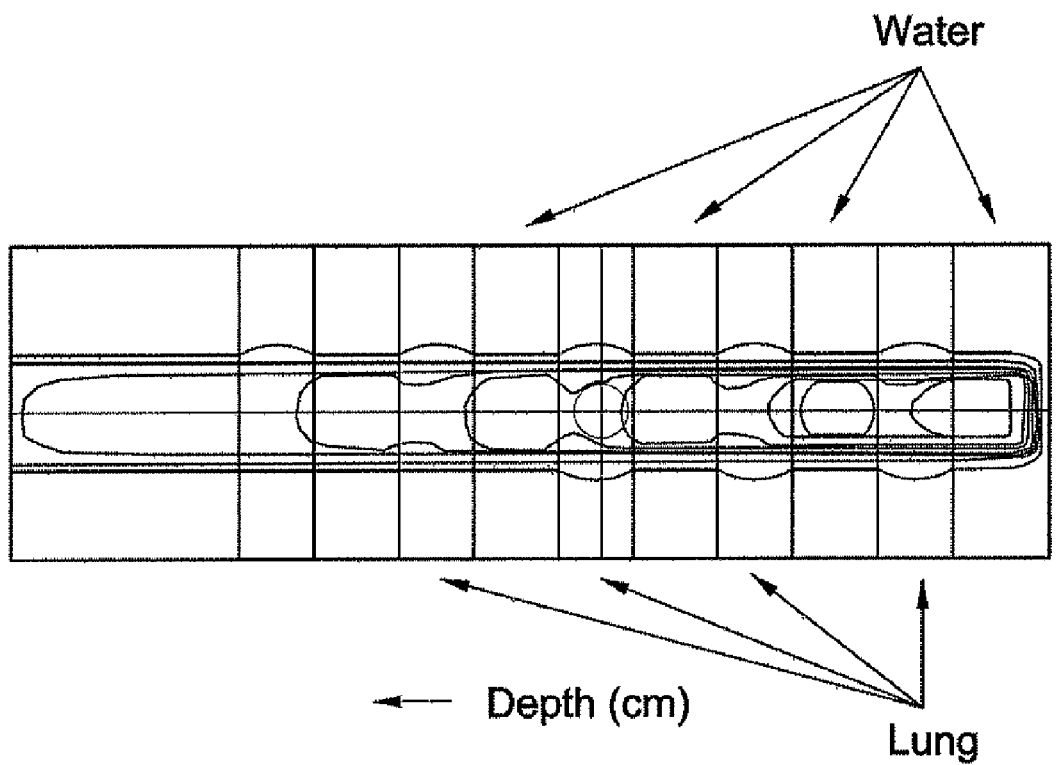
Figure 7:
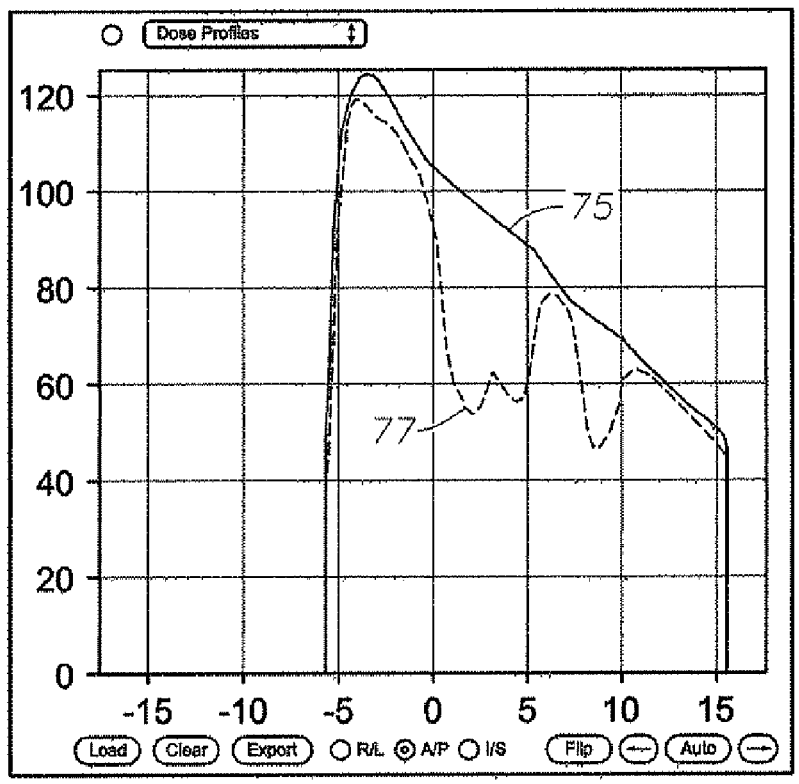
FIG. 7 is a graph diagram illustrating a comparison between calculated dose using the traditional pencil beam model and a calculated dose provided by a Monte Carlo simulation for a 10×15 mm field in real lung as derived from a patient's CT scan.

Lateral disequilibrium, most prominent for small beam fields, low electron density media, and high delivery energy, results when there are an unequal number of charged particles entering and exiting a region on the central axis of the pencil beam. FIGS. 5 and 6 illustrate a comparison between calculated dose (dose plot 71) using the traditional pencil beam model, described above, and a calculated dose (dose plot 73) provided by a Monte Carlo simulation for a 3×3 cm field in a phantom having alternating layers of water and lung. FIG. 7 illustrates a comparison between calculated dose (dose plot 75) using the traditional pencil beam model and a calculated dose (dose plot 77) provided by a Monte Carlo simulation for a 10×15 mm field in lung. Embodiments of the system 30 and methods include determining central axis primary dose for each pencil beam having a field size r in a medium having an electron density ρ from a central axis primary dose model for water equivalent medium of an equivalent effective field size ρ·r, i.e., r'=ρ·r. According to an embodiment of the system 30 and method, this can include determining central axis primary dose by modifying a two-dimensional radiological kernel representing electron transport so that a central axis dose implied by the kernel is substantially equivalent to a central axis dose in water of an equivalent pencil beam field size substantially equal to a desired field size multiplied by a ratio of electron density of the homogeneous medium to electron density of water such that:

$N_\rho(x,y)$=Rect(x/w,y/h)Radiological$_\rho(r)$Geometric (r), and

Radiological$_\rho(r)=(\rho/2\pi)*(c\gamma_1\exp(-\gamma_1\cdot\rho\cdot r)+(1-c)\gamma_2\exp(-\gamma_2\rho\cdot r)$, where $N_\rho(x,y)$ is referred to interchangeably as a two-dimensional primary dose profile or penumbra, Radiological$_\rho(r)$ represents a kernel equation, and ** refers to a two-dimensional convolution.

Similarly, embodiments of the system 30 and methods include determining a central axis scatter dose for each pencil beam having a field size r in a medium having an electron density ρ from a central axis scatter dose model for water equivalent medium of an equivalent effective field size ρ·r. According to an embodiment of the system 30 and method, this can include performing a modified Clarkson integration whereby central axis dose in the medium is derived from the central axis dose of water for an equivalent field size ρ·r. equal to the field size of the pencil beam multiplied by a ratio of an electron density of the medium to an electron density of water such that:

$$S_\rho(x, y, d) = \frac{1}{2\pi}\int_0^{2\pi} S(\rho\cdot r(\theta), d)d\theta.$$

Figure 8:
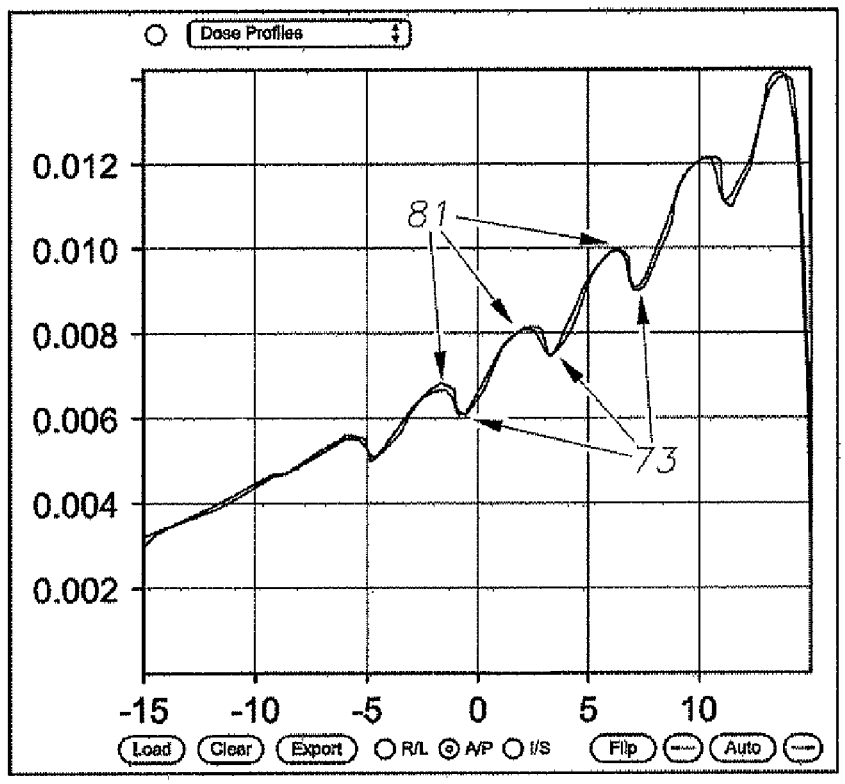
FIGS. 8 and 9 are graph diagrams illustrating a comparison between calculated dose using the enhanced pencil beam model and a calculated dose provided by a Monte Carlo simulation for the 3×3 cm filed in a phantom having alternating layers of water and lung, according to an embodiment of the present invention.
Figure 9:
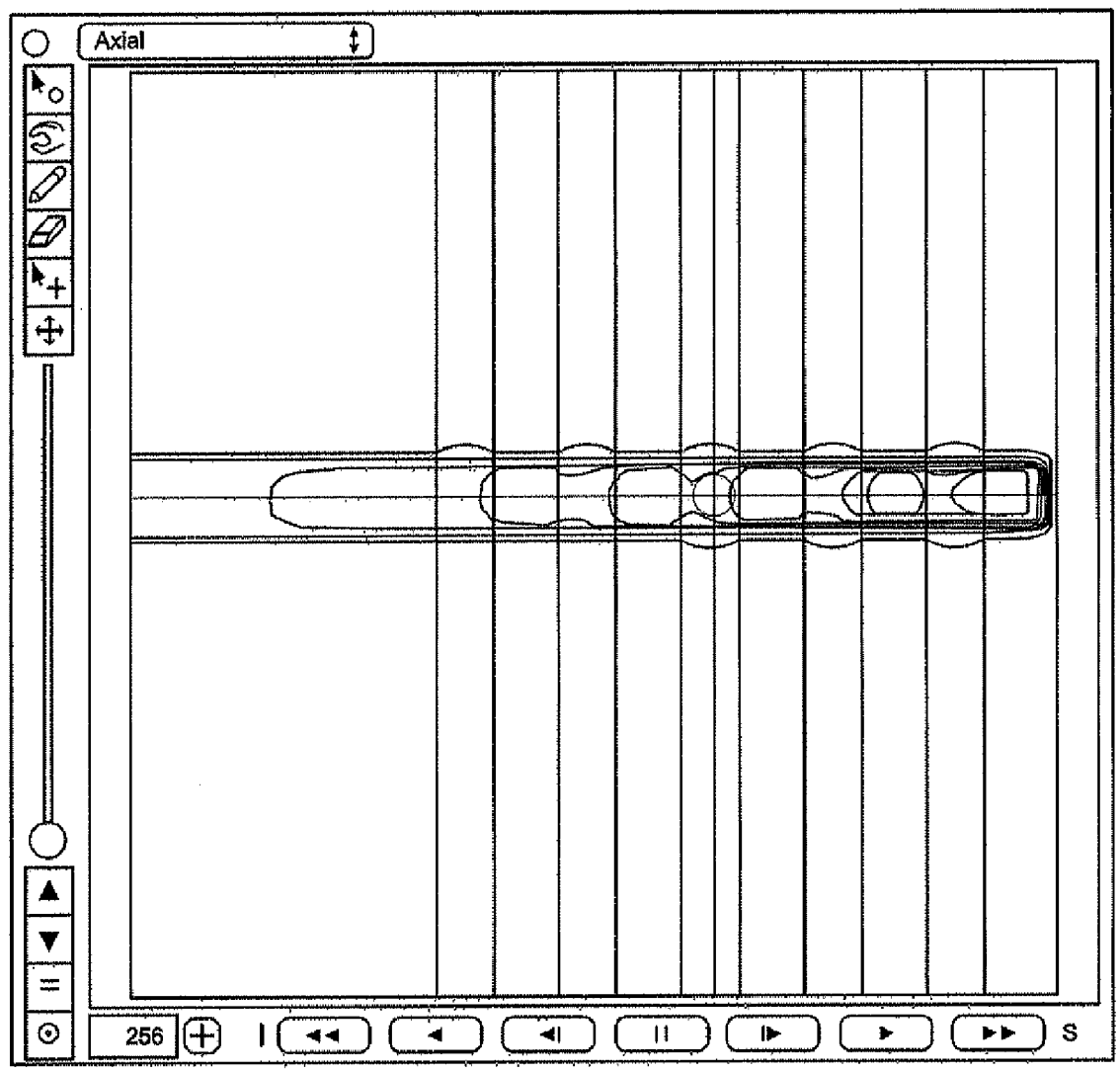
Figure 10:
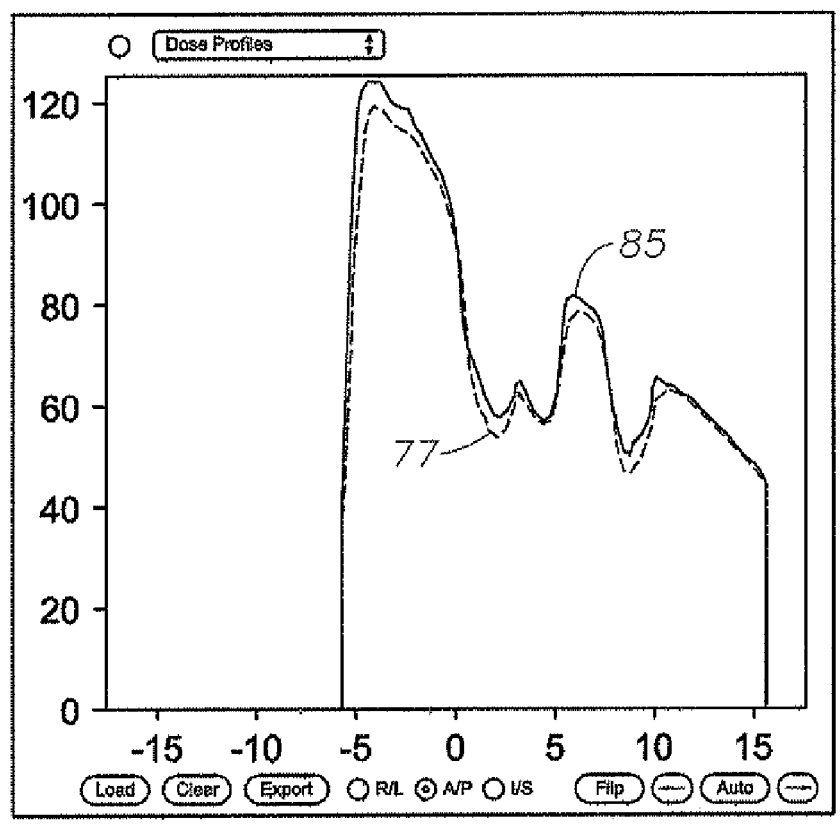
FIG. 10 is a graph diagram illustrating comparison between calculated dose using the enhanced pencil beam model and a calculated dose provided by a Monte Carlo simulation for a 10×15 mm field in lung, according to an embodiment of the present invention.

FIGS. 8 and 9 illustrate a comparison between calculated dose (dose plot 81) using the enhanced pencil beam model, described above, and a calculated dose (dose plot 73) provided by a Monte Carlo simulation for the 3×3 cm field in a phantom having alternating layers of water and lung. FIG. 10 illustrates a comparison between calculated dose (dose plot 85) using the enhanced pencil beam model and a calculated dose (dose plot 77) provided by a Monte Carlo simulation for a 10×15 mm field in lung. A more detailed description follows of the modeling, particularly with respect to lateral disequilibrium. As will be described later, the $N_\rho(x,y)$ and $S_\rho(x,y,d)$ profiles can be stored, for example, in three-dimensional primary and scatter tables, respectively, for each of a representative plurality of densities to formulate a machine-specific portion of the model.

Figure 11:
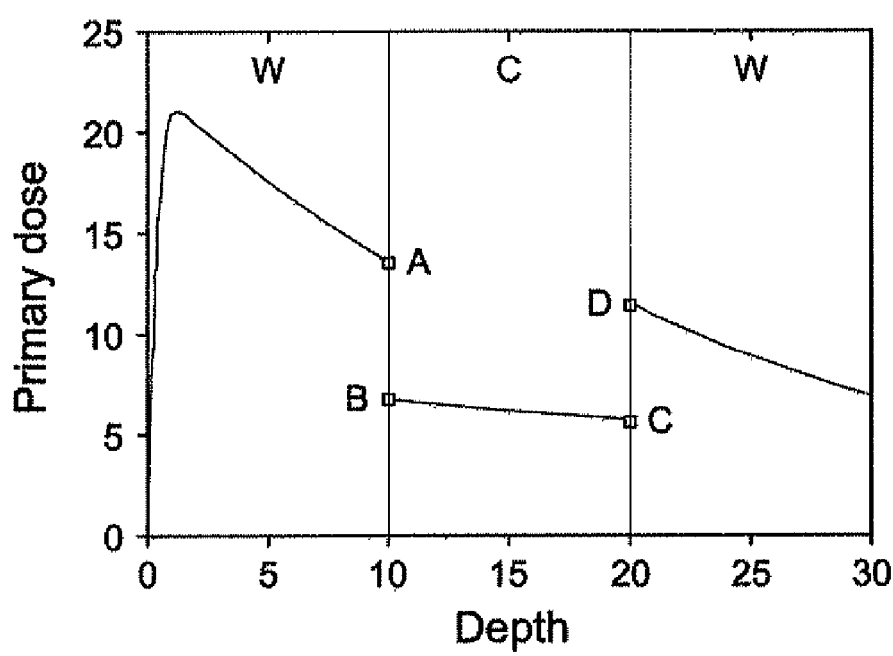
FIG. 11 is a graph diagram illustrating the behavior of the central axis (CAX) equilibrium primary dose (also referred to as equilibrium dose to a homogeneous medium having the same density) for a narrow 6 MV photon beam which is incident on a layered medium composed of water-like, lung-like and again water-like materials, each 10 cm thick.

In a more specific model, according to an embodiment of the present invention, the parameters the linear attenuation coefficient μ, the longitudinal build-up coefficient β, and the lateral build-up coefficient γ are material and beam energy, i.e., beam quality, dependent. Moving from one medium to another, the equilibrium factor E(r), described previously, varies depending on the beam radius and the next medium's lateral build-up coefficient γ, which is inversely proportional to the electron range, which is the average distance traveled by an electron after interacting with a primary photon. FIG. 11 illustrates the behavior of the central axis (CAX) equilibrium primary dose for a narrow 6 MV photon beam which is incident on a layered medium composed of water-like, lung-like and again water-like materials, each 10 cm thick. This equilibrium factor is like primary dose, but does not smoothly build-up and build-down around interfaces. It instead takes the value that would be appropriate given no interface. The factor is useful in calculating primary dose. It can be seen that the density of the material effects dose. Thus, the parameters of the model should be resealed based on the density of the medium.

Figure 12:
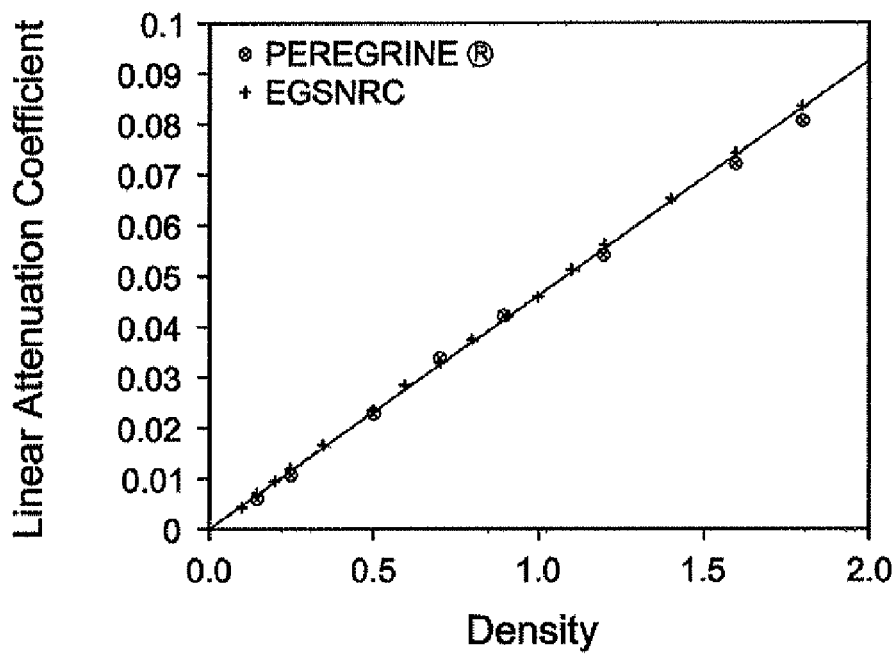
FIG. 12 is a graph diagram illustrating the linear attenuation coefficient as a function of the density as derived from a Monte Carlo simulation with the Electron Gamma Shower Monte Carlo simulation package by the National Research Council in Canada (EGSNRC) and PEREGRINE®.
Figure 13:
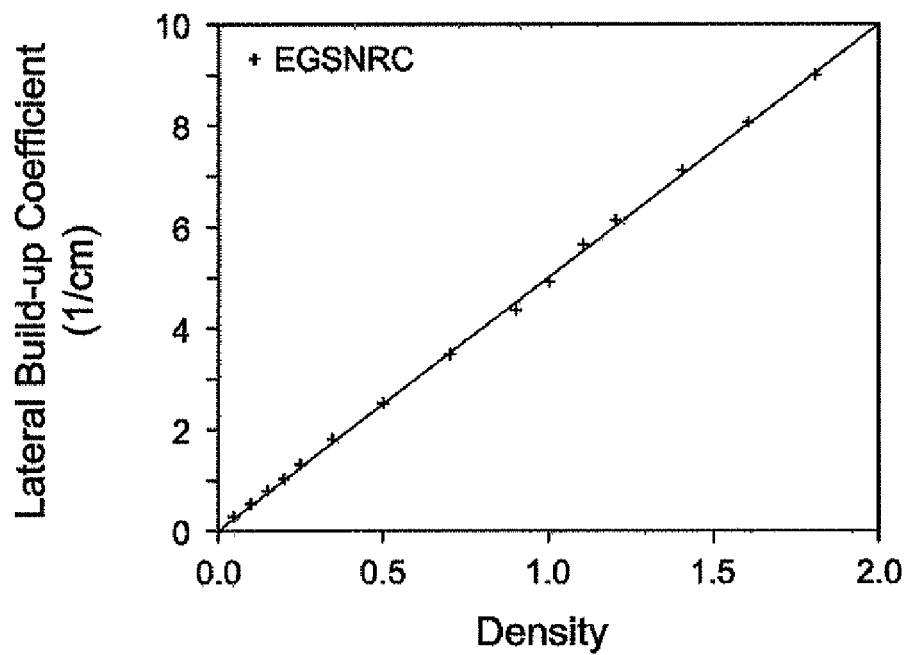
FIG. 13 is graph diagram illustrating the lateral buildup coefficient as a function of the density as derived from a Monte Carlo simulation with EGSNRC and PEREGRINE®.

As described above, the beam radius r in the CAX primary dose equation is replaced with an effective radius equal to the beam radius times the density of the medium at a given point. The initial parameterization of the model can be performed for a homogeneous medium, in particular, for water, so that all densities can be given relative to water. In particular, the linear attenuation coefficient $\mu$, the longitudinal build-up coefficient $\beta$, and the lateral build-up coefficient $\gamma$ can be rescaled in direct proportionality to the density. So for an arbitrary density $\rho$ at depth d, the effective beam radius r can be replaced by $\rho r$ such that:

$$\mu(d) = \mu_0 \rho(d),$$

$$\beta(d) = \beta_0(\rho(d)r)\rho(d),$$

$$\gamma(d) = \gamma_0 \rho(d),$$

where the subscript 0 corresponds to water, and water's density is taken as unity. The longitudinal build-up coefficient $\beta$ has a substantial dependence on field size, especially for narrow beams. The scalability of the parameterization as a function of the density has been verified using Monte Carlo simulations, as illustrated in FIGS. 12 and 13. FIG. 12 illustrates the linear attenuation coefficient $\mu$ as a function of the density. FIG. 13 illustrates the lateral build-up coefficient $\gamma$ as a function of the density.

According to this particular methodology, the dose at point i can be calculated, for example, using the following expression:

$$D_i(r,d) = ISC \cdot F(r) \cdot [P(r,d) \cdot N(r,d) + S(r,d)].$$

Because of the linearity of $\mu$ and $\beta$ with the density, the behavior of central axis primary dose can be calculated using the equation:

$$P(r,d) = P_0^c(r,d)[1 - \exp(-\beta d_{\mathit{eff}})] \exp(-\mu d_{\mathit{eff}}),$$

where $\mu_0$ is the linear attenuation coefficient for primary radiation in water and $d_{\mathit{eff}}$ is the radiological depth, described previously. The normalization factor $P_0(r,d)$ which performs the same function as Radiological$_\rho(r)$, described previously, can be modeled by the equation:

$$P_0(r,d) = P_{eq}[1 - a \exp(-\gamma_1(d)r) - (1-a)\exp(-\gamma_2(d)r)],$$

where $P_{eq}$ is a global normalization factor. This parameterization is as accurate for water as that provided by the traditional pencil beam model, but more accurate for low density regions such as in lung by accounting for reduced actual dose and wider penumbra resulting from lateral electronic disequilibrium.

Similarly, central axis scatter dose for water-like media can be parameterized as:

$$S(d,r) = \{S_{surf}(r) + [S_0(r) - S_{surf}(r)][1 - \exp(-\delta(r)d)]\} \exp(-\mu d),$$

where $S_{surf}(r)$ is a scatter dose surface term, $S_0(r)$ is a normalization factor, and $\delta(r)$ is a scatter build-up coefficient that are each field-size dependent. This approximation works well due to the slow variations on scatter with position.

As noted previously, the traditional pencil beam model also does not account for multiple dose build-up and dose build-down due to the complex electron density distribution/continuous density changes of the human body. According to an embodiment of the system 30 and methods, the dose build-up and dose build-down regions in the depth-dose curve can be modeled via a central axis convoluting method by solving numerically the following differential equations:

$$\frac{dP_0^c}{dx} = \rho\beta[P_0(x) - P_0^c(x)],$$

where $P_0(d) = N_{\rho(d)}(0,0)$ is the equilibrium central axis primary dose for a point on the central axis at depth d; and $$\frac{dS_0^c}{dx} = \rho\delta(x)[S_0(x) - S_0^c(x)],$$

where $S_0(d) = S_{\rho(d)}(0,0,d)$ is the equilibrium central axis scatter dose for a point on the central axis at depth d. The convoluted version of $P_0(x)$ is $P_0^c(x)$ can be used to satisfy the differential equation $dP_0^c(x)/dx$, and the convoluted version of $S_0(x)$ is $S_0^c(x)$ can be used to satisfy the differential equation $dS_0^c(x)/dx$.

Where the beam field is being described with respect to a radius r, these equations can be modeled alternatively as:

$$\frac{dP_0^c}{dx} = \beta(x)[P_0(x,r) - P_0^c(x,r)], \text{ and}$$

$$\frac{dS_0^c}{dx} = \delta(x)[S_0(x,r) - S_0^c(x,r)]$$

where $$\frac{dP_0^c}{dx} \text{ and } \frac{dS_0^c}{dx}$$

convolute the step-like variations of $P_0(x,r)$ and $S_0(x,r)$, respectively, that are due to the rapid variations in density with the medium dependent dose build-up and dose build-down processes. Here x denotes depth, $P_0(x,r)$ and $S_0(x,r)$ are the convoluted values of the normalization factor for primary and scatter dose, respectively, and $\beta(x)$ and $\gamma(x)$ are the position dependent build-up coefficients. The convoluted version of $P_0(x)$ is $P_0^c(x)$ can be used to satisfy the differential equation d $P_0^c(x)/dx$, and the convoluted version of $S_0(x)$ is $S_0^c(x)$ can be used to satisfy the differential equation d $S_0^c(x)/dx$. Both sets of differential equations provide a generalized solution for modeling dose due to the multiple dose build-up and dose build-downs.

In practice, however, the values for the density, typically estimated from the patient CT scans, tend to vary rapidly from voxel to voxel. As such, a discrete solution to the differential equations is preferable. The simplest solution to the discrete version of the differential equation d $P_0^c(x)/dx$ is given by $$P_0^c(i+1) = P_0^c(i) + h\beta(i)[P_0(i) - P_0^c(i)],$$

where the index i corresponds to depth $d(i) = ih$, and h is the discretization step in a homogeneous grid, and the initial condition is $P_0^c(0) = 0$.

Other solutions to solve the differential equations can include, for example, the use of a second and a fourth order Runge-Kutta differential equation solvers. The second-order Runge-Kutta differential equation solver is given by:

$$P_0^c(i+1)=P_0^c(i)+K_2(i),$$

where $K_1(i)=h\beta(i)[P_0(i)-P_0^c(i)]$, and $$K_2(i)=h[\beta(i)+\beta(i+1)]/2 \cdot [P_0(i)/2+P_0(i+1)/29 -P_0^c(i)-K_1(i)/2],$$

where the values for $\beta(x_i+h/2)$ and $P_0(x_i+h/2)$ are approximated as the average between their respective values at points i and i+1. This discretization error is proportional to the cube of the mesh step.

Using the same approximation for $\beta(x_i+h/2)$ and $P_0(x_i+h2)$, the fourth order Runge-Kutta differential equation solver is given by:

$$P_0^c(i+1)=P_0^c(i)+K_1(i)/6+K_2(i)/3+K_3(i)/3+K_4(i)/6,$$

where $K_3(i)=h[\beta(i)+\beta(i+1)]/2 \cdot [P_0(i)/2+P_0(i+1)/2-P_0^c(i)-K_2(i)/2]$, and $K_4(i)=h\beta(i+1)[P_0(i+1)-P_0^c(i)-K_3(i)]$. Here the discretization error is proportional to the fifth power of the mesh step.

According to an embodiment of the system 30 and methods, dose profiles, including off-axis ratios, can be calculated using a density-dependent kernel using, for example, the equation for $P_0(r,d)$, described previously, and then evaluated using the profiles corresponding to the local value of the density at a given point, using the equation given by:

$$P(x,y)=Rect(x/w,y/h)Geometric(x,y)Radiological_\rho(r).$$

Around media boundaries for other change density regions, profiles can be obtained by a linear combination of local and previous ones. Using two penumbra/profiles, for example, the dose, on and off axis, can be modeled as:

$$N(x,y,d)=(1-w(d))N_{\rho(d)}(x,y)+w(d)N_{\rho_{prev}(d)}(x,y), \text{ or}$$

$$N(x,y,d)=(1-w(d))N(x,y,d,\rho)+w(d)N(x,y,d,\rho_{prev}),$$

where the weight w(d) is selected or otherwise determined by consistency so that the resulting dose profile provides a value substantially equal to a convoluted value of the central axis dose at the current or local depth when a point of interest applied to the linear combination at the current or local depth is on the central axis, i.e., weight w(d) can be selected so that $P_0^c(d)$ equals $N(0,0,\rho)$; and where $N_{\rho(d)}(x,y)$ and $N(x,y,d,\rho)$ represent the local profile and $N_{\rho_{prev}(d)}(x,y)$ and $N(x,y,d,\rho_{prev})$, represent the profile taken at the density of a previous depth, i.e., depth closer to the surface.

Similarly, scatter profiles can be obtained in a similar fashion as that of the primary or by employing an effective density $\rho'(d)$ in the following equation model:

$$S(x,y,d)=S_{\rho'}(x,y,d), \text{ or}$$

$$S(x,y,d)=S(x,y,d,\rho'),$$

where the effective density $\rho'(d)$ is selected or otherwise determined by consistency so that the resulting scatter dose profile provides a value substantially equal to a convoluted value of the central axis scatter dose at the current or local depth when the point of interest is on the central axis, i.e., can be selected so that $S^C(d)$ equals $S(0,0,d, \rho'(d))$.

Figure 19:
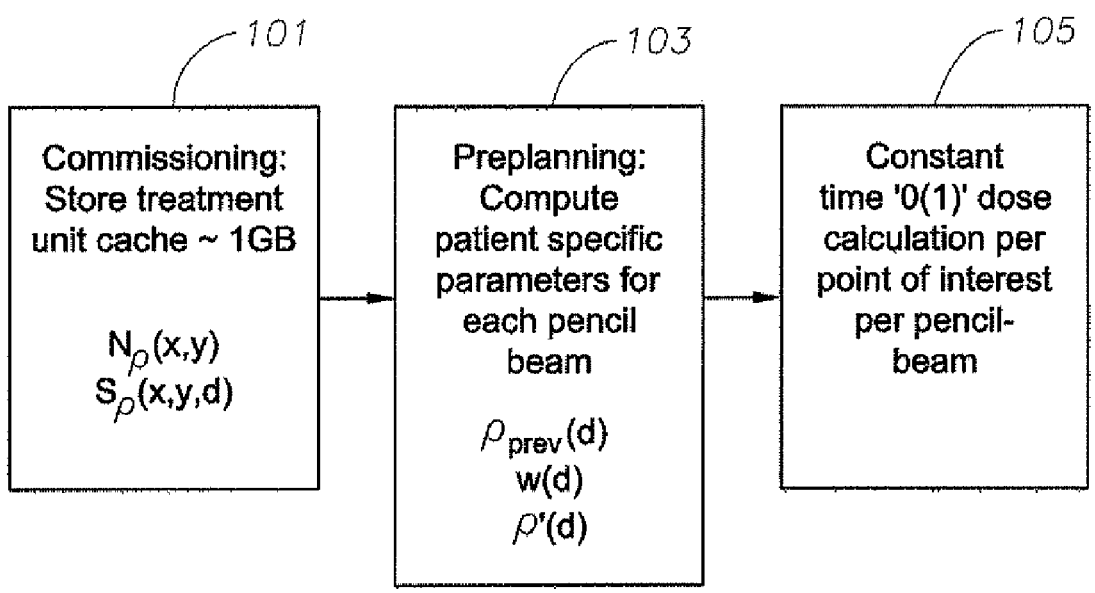
FIG. 19 is a schematic diagram illustrating a workflow to determine dose in media of varying density from a high-energy radiation-beam for radiation treatment according to an embodiment of the present invention.
Figure 20A:
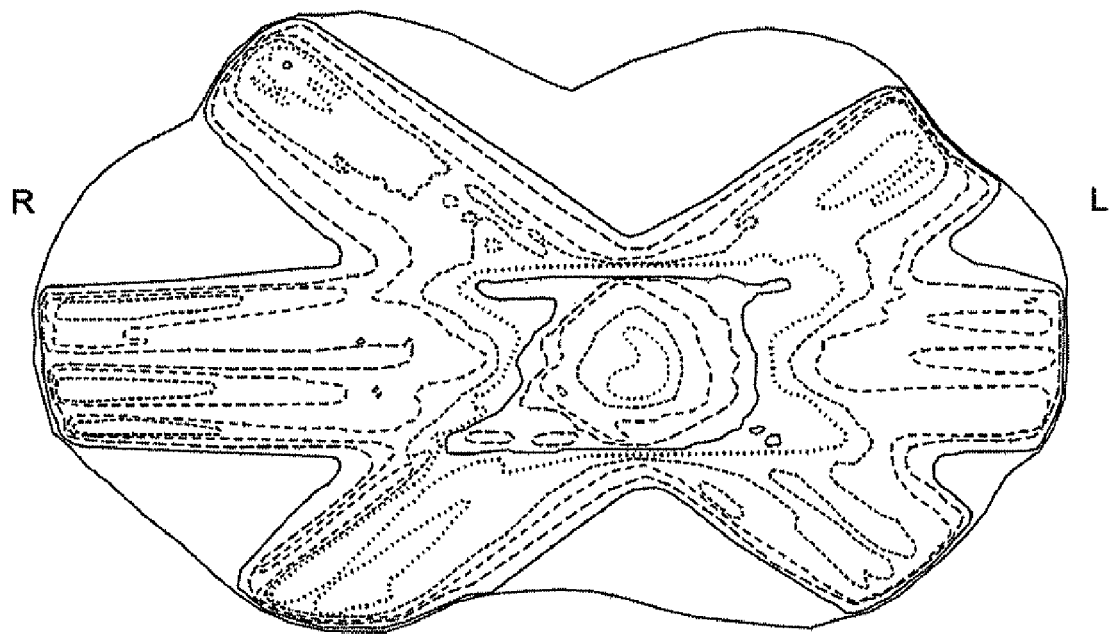
Figure 20B:
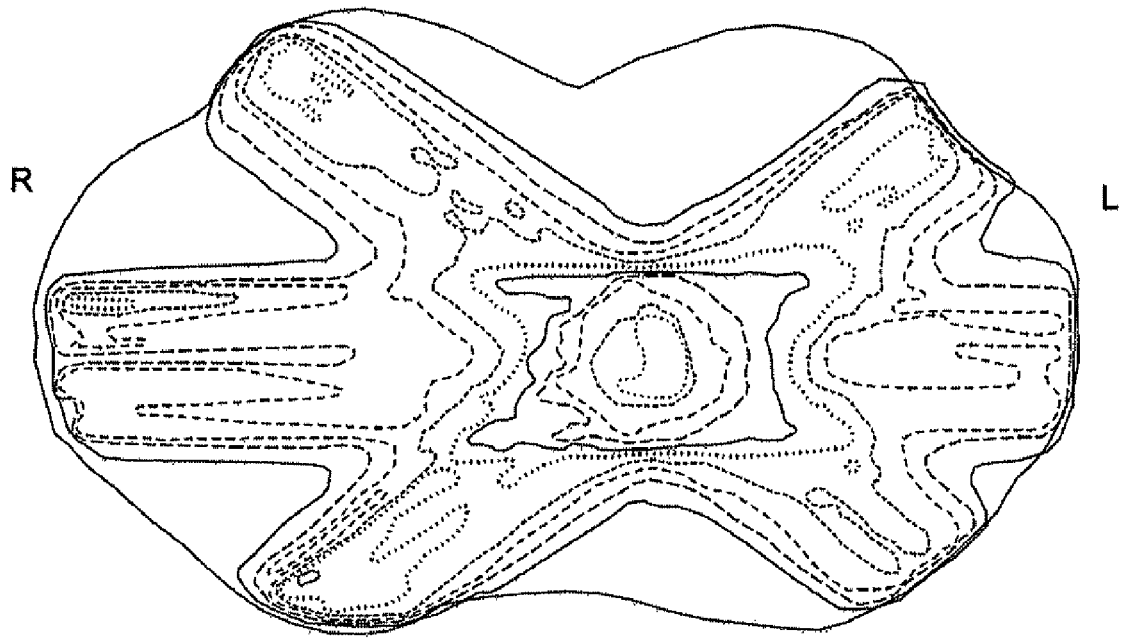
Figure 22:
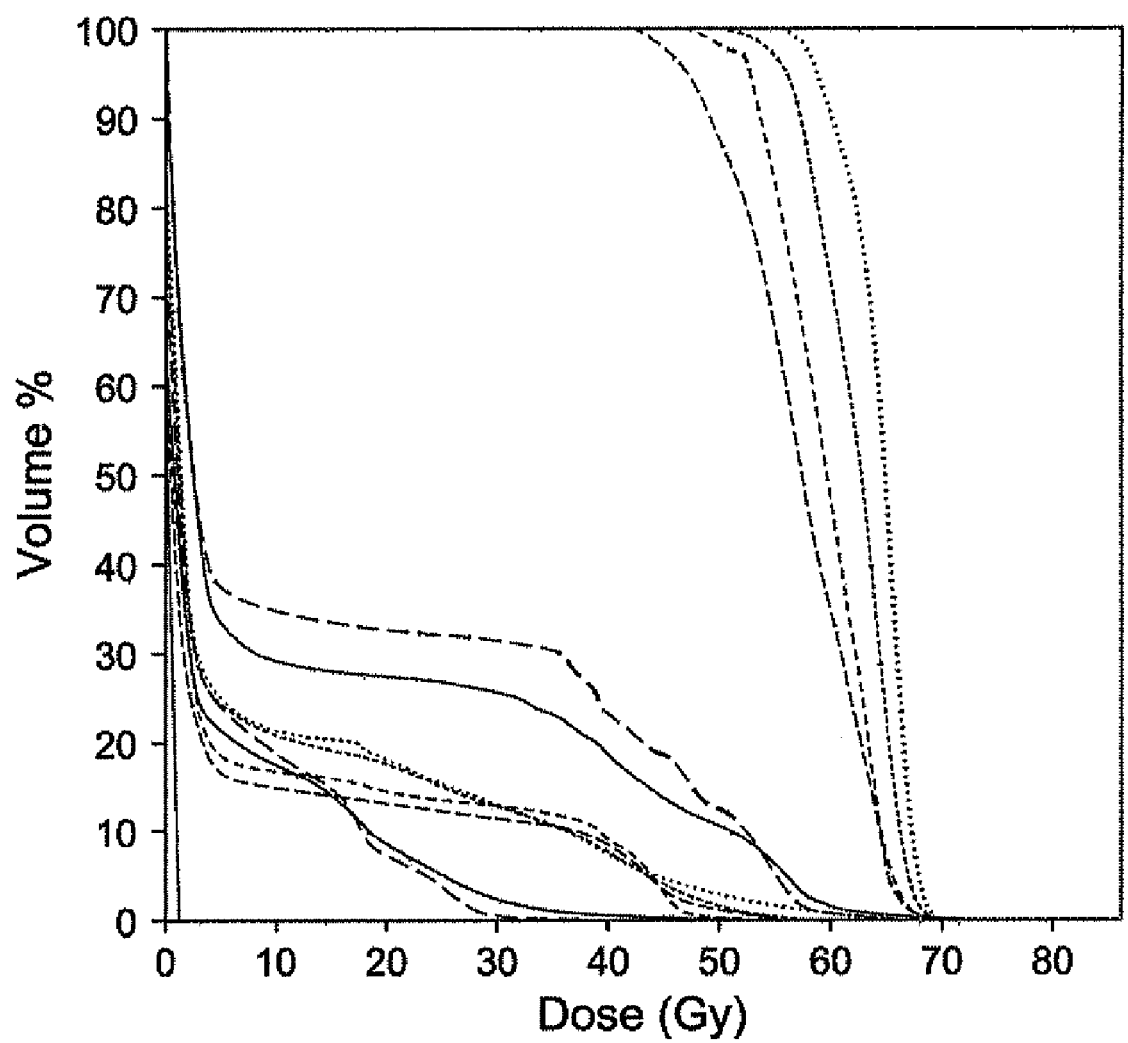
Figure 23:
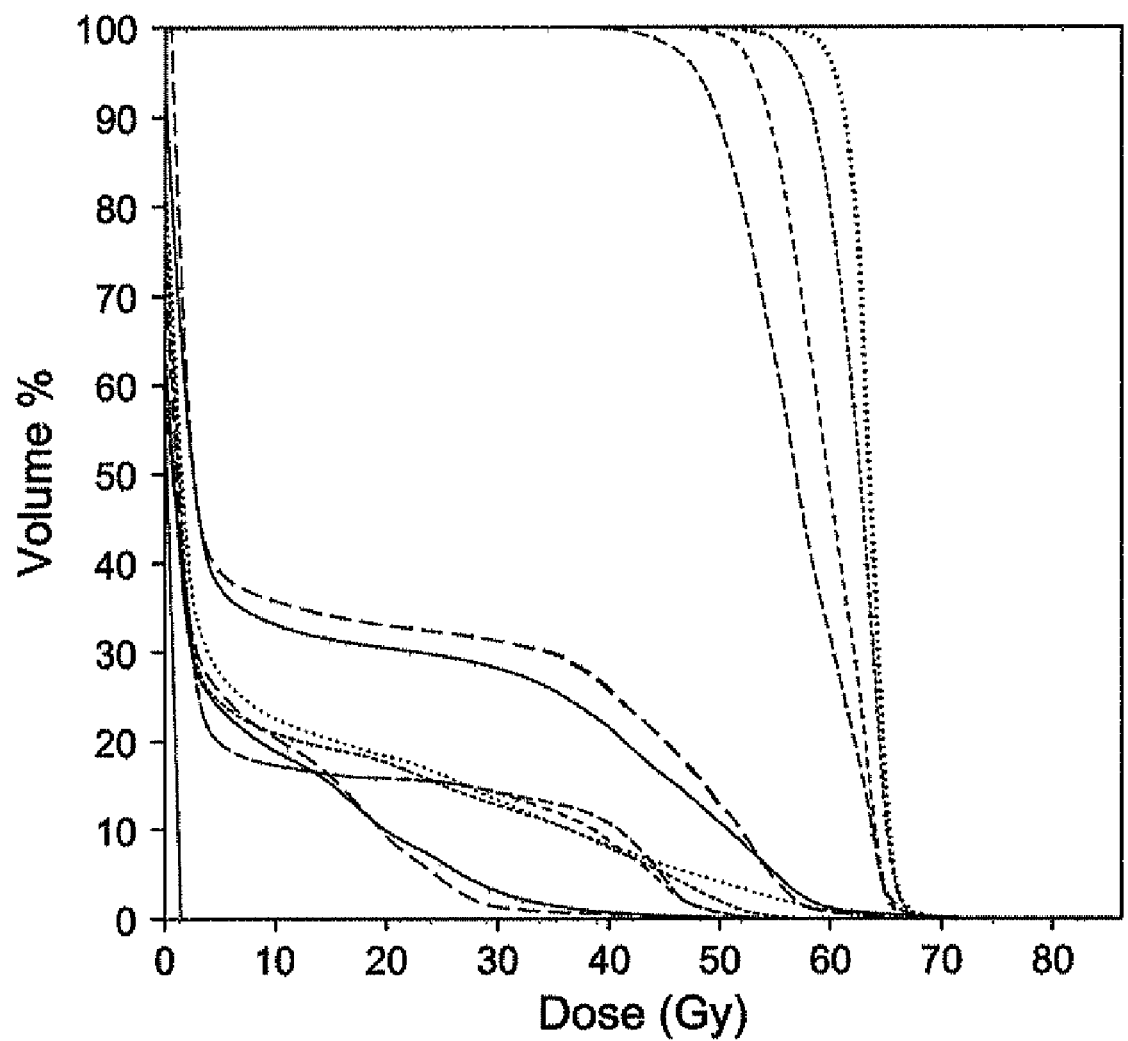
Figure 24:
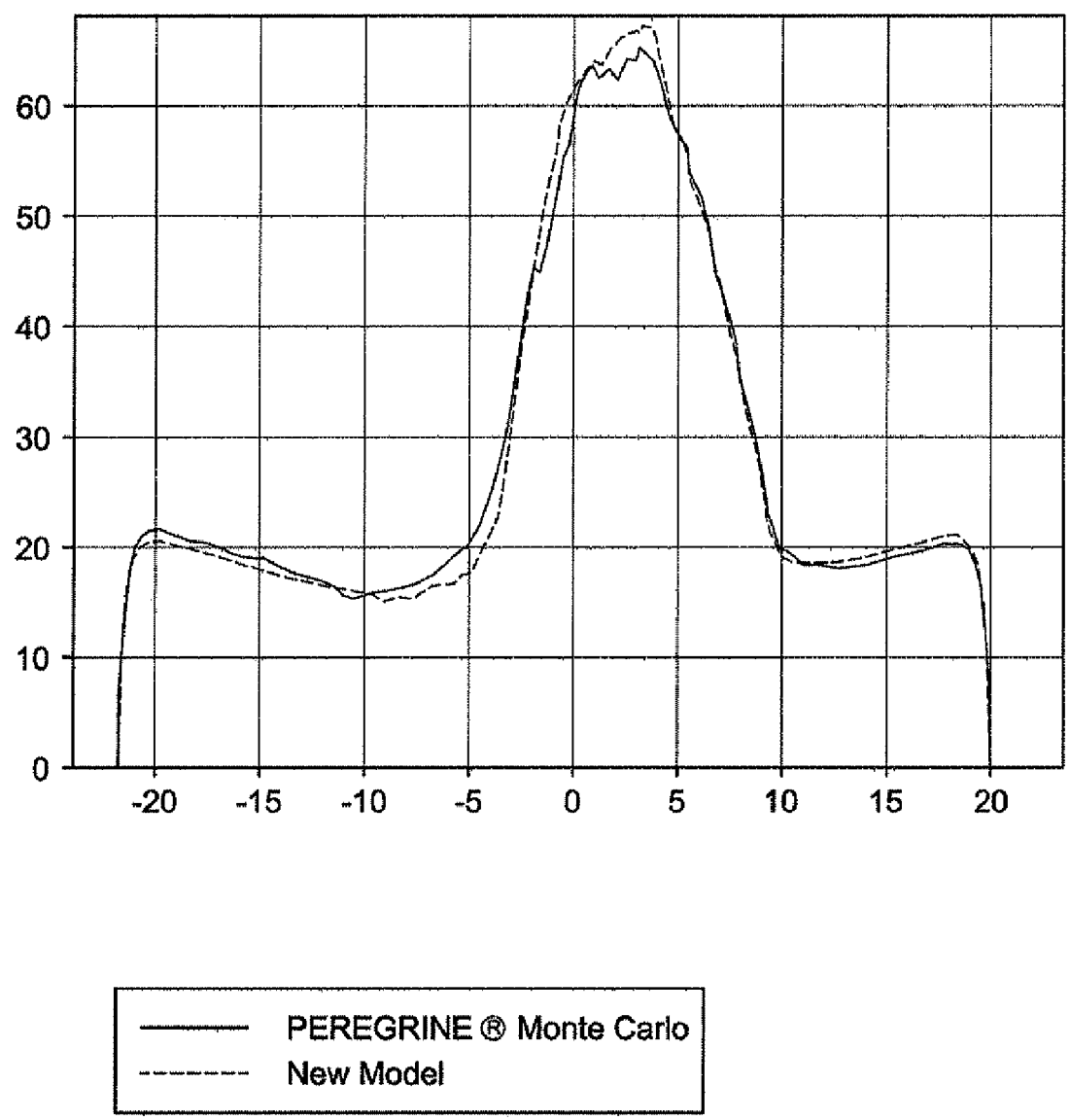

According to an embodiment of the system 30 and methods, central axis primary and scatter dose for each FSPB is stored in database 61. According to another embodiment, central axis primary and scatter dose profiles for a plurality of densities and the $\rho_{prev}(d)$, w(d), and $\rho'(d)$ for each beam field to be used in the treatment plan is stored in the database 61 (as shown in FIG. 19). In a clinical situation, every beamlet going through the patient will see a different distribution of densities, thus, each dose profile solution will be different. These values can be quickly pre-computed and stored for future use in one of the dose calculation equations.

Figure 14:
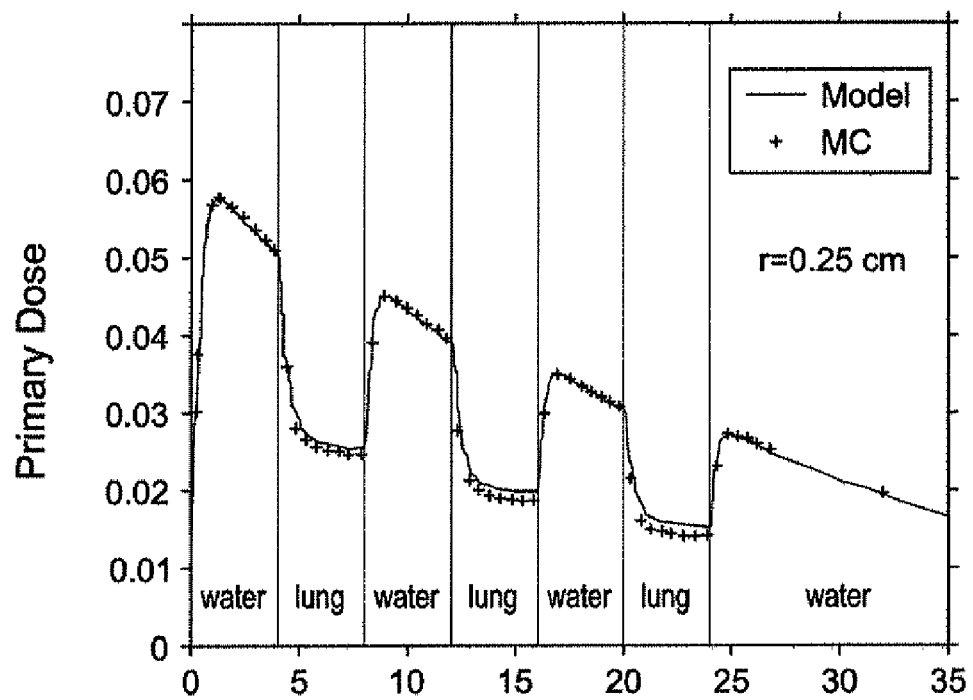
FIG. 14 is a graph diagram illustrating the results of a modeling of primary dose for an alternating water-lung slab phantom with thickness 4 cm for a 6 MV x-rays beam of radius 0.25 cm according to an embodiment of the present invention where MC indicates Monte Carlo simulation with EGSNRC.
Figure 15:
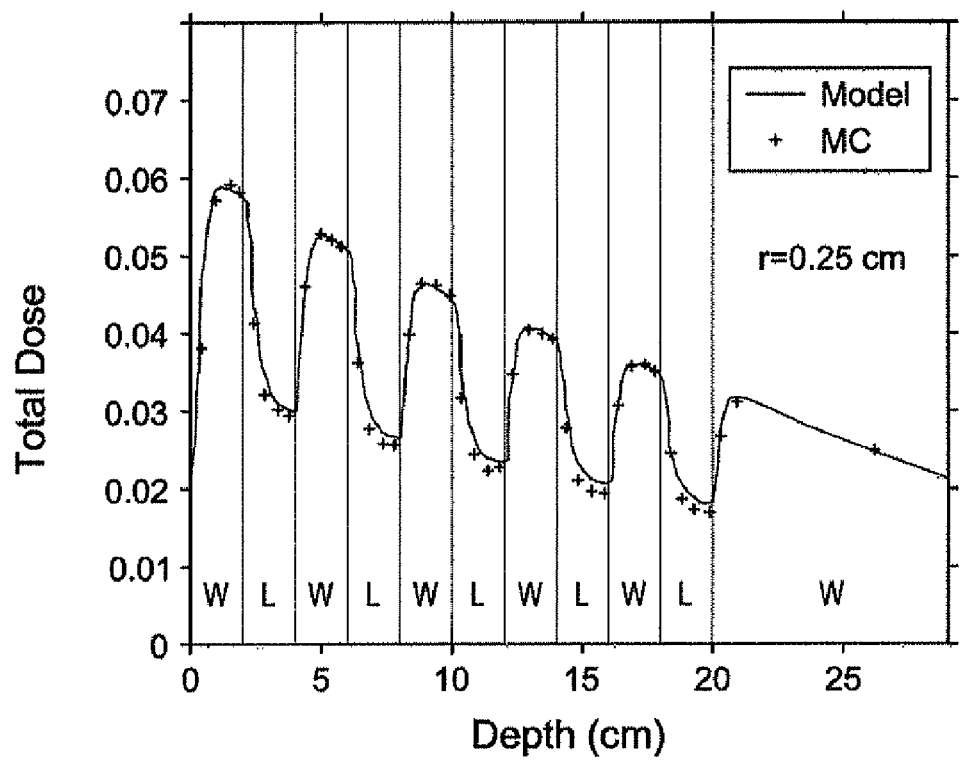
FIG. 15 is a graph diagram illustrating the results of a modeling of primary dose for an alternating slab geometry, but with thickness 2 cm, for a 6 MV x-rays beam of radius 0.25 cm according to an embodiment of the present invention where MC indicates Monte Carlo simulation with EGSNRC.
Figure 16:
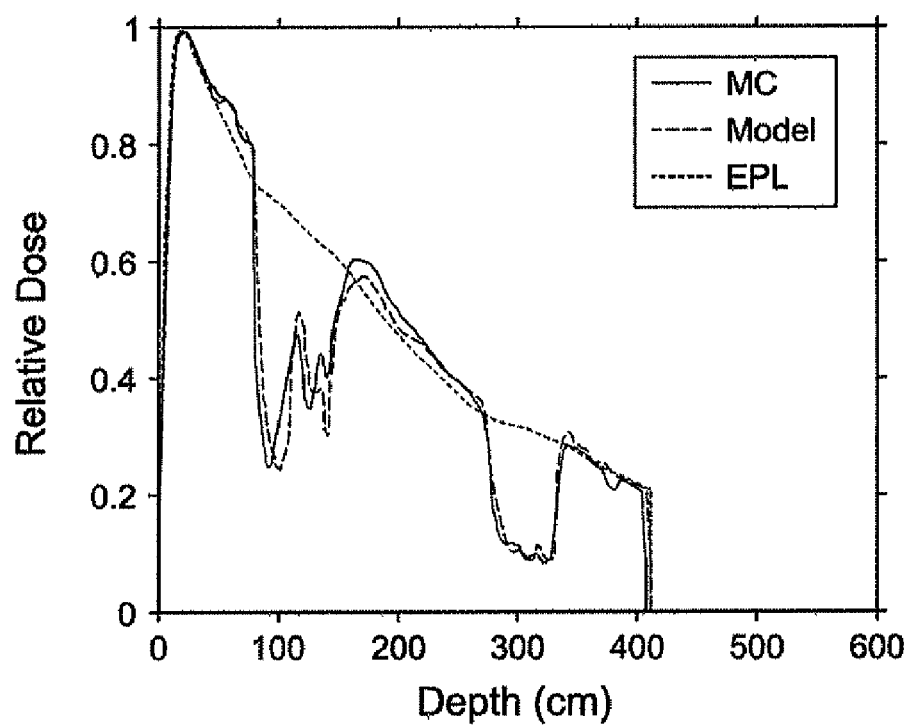
FIG. 16 is a graph diagram illustrating a comparison of primary dose calculated using PEREGRINE® Monte Carlo (MC), effective path-length (EPL), and the enhanced pencil beam model for a 0.5 cm by 0.5 cm 6 MV x-ray FSPB traversing a patient according to an embodiment of the present invention.

FIGS. 14-16 illustrate the application of enhanced pencil beam model for heterogeneous media. FIG. 14 illustrate the results of a modeling of primary dose for an alternating water-lung slab phantom with thickness 4 cm for a 6 MV x-rays beam of radius 0.25 cm, whereby the dimensions involved allow the beam to achieve longitudinal electron equilibrium. FIG. 15 shows the results of a modeling of primary dose for an alternating slab geometry, but with thickness 2 cm, for a 6 MV x-rays beam of radius 0.25 cm so that electronic equilibrium is almost never achieved. Finally, FIG. 16 presents a comparison of primary dose calculated using Monte Carlo (MC), effective path-length (EPL), and the enhanced pencil beam model (Model) for a 0.5 cm by 0.5 cm 6 MV x-ray FSPB traversing a patient. Note, the broader dips in dose correspond to lung regions. The agreement between the new model and Monte Carlo results is remarkable, while the traditional radiological path-length method grossly overestimates dose in lung regions.

Figure 17:
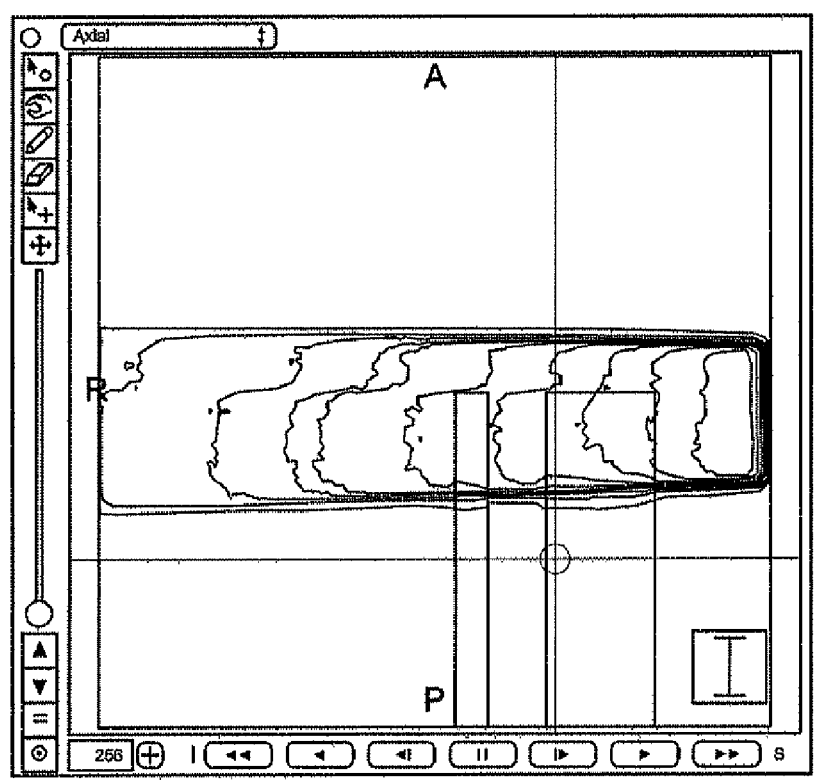
FIG. 17 is a graph diagram illustrating a semi-slab phantom composed of water and lung with a 7 cm by 7 cm 6 MV x-ray beam incident from the left according to an embodiment of the present invention.
Figure 18:
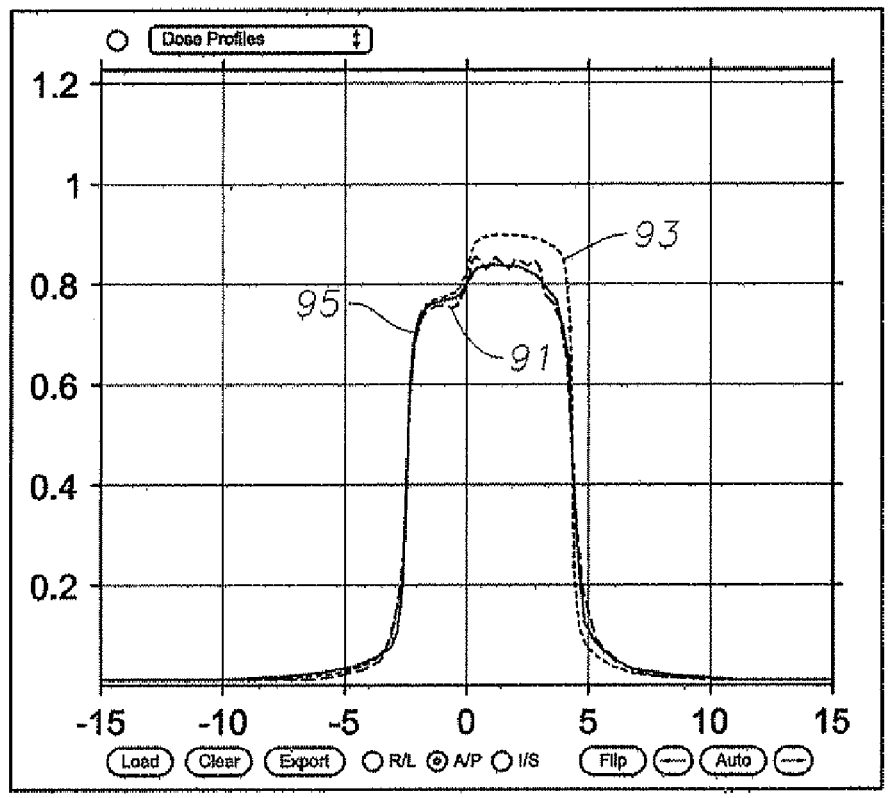
FIG. 18 is a graph diagram illustrating a comparison between total dose calculated using Monte Carlo, effective path-length, and the new FSPB model for the two density semi-slab phantom shown in FIG. 17.

As noted previously, the traditional pencil beam model also does not account for variations in electron density across the beam front or lateral heterogeneities. The FSPBs can experience various regions in a complex medium, e.g., human body, where the electron density distribution varies laterally along a plane perpendicular to a depth of interest associated with a point of interest. FIG. 17 illustrates a semi-slab phantom composed of water (in black) and lung (in grey) with a 7 cm by 7 cm 6 MV x-ray beam is incident from the left. The isodose lines shown were calculated using Monte Carlo. According to the exemplary embodiment, the new model provides the enhanced accuracy by determining an off-axis dose profile for a pencil beam to a point of interest of the complex medium by using an off-axis dose profile of the pencil beam at the depth of interest corresponding to the electron density distribution substantially equal to that of a local electron density distribution near the point of interest. That is, the model can assume that the density distribution inside the beam field equals that of the density at or near the point of interest, to thereby enhance the modeling of the dose. FIG. 18 shows a comparison between total dose 91 calculated using Monte Carlo, traditional effective path-length (EPL), and new FSPB model according to an embodiment of the present invention for the two density semi-slab phantom shown in FIG. 17. The calculations for the traditional effective path-length (EPL) model and new model were performed by superimposing 0.5 cm by 0.5 cm FSPBs. FIG. 18 again illustrates the agreement between Monte Carlo and the new model and the significant differences between Monte Carlo and the traditional effective path length model.

As perhaps best shown in FIG. 19, the system 30 and methods include performing a workflow to determine dose in heterogeneous media of varying density from a therapeutic high-energy radiation-beam for radiation treatment. Beneficially, the workflow can be applied to determine dose according to various planning-analytical methodologies including inverse planning, forward plan dose calculation, interactive dose calculation, and others. Also beneficially, the modeling of the parameters developed during the workflow can be applied to not only photons, but also electrons and protons. Also, due to physical and mathematical similarities, the methods can also be applied to the calculation of neutron dose in heterogeneous media.

The workflow generally includes performing the steps or operations of predetermining a delivery machine-dependent representation of radiation dose for a plurality of different electron densities selected over a preselected representative range (block 101), predetermining a depth-dependent representation of central axis properties of a pencil beam passing through a complex medium having a complex spatial distribution of heterogeneous electron densities for each of a plurality of pencil beams (block 103), and determining with constant time computational complexity radiation dose for each of a plurality of points of interest in the complex medium by applying the predetermined machine-dependent and depth-dependent representations (block 105).

The step or operation of predetermining a delivery machine-dependent representation of radiation dose can include the steps of receiving a set of photon beam data for a water medium to thereby parameterize a dose model for unit density; parameterizing a machine-dependent dose model for unit density responsive to the set of photon beam data; determining a machine-dependent primary dose profile for each of a first set of a plurality of electron densities distributed through a preselected range of densities responsive to the dose model for unit density to provide off-axis data for the range of densities; and determining a machine-dependent scatter dose profile for each of a second set of a plurality of electron densities distributed through a preselected range of densities responsive to the dose model for unit density.

According to the exemplary embodiment, the primary and scatter dose profiles are each at least a two-dimensional primary dose profile, but preferably a three or four dimensional primary dose profile and cover a representative portion of potential electron densities for a plurality of media. For example, the primary dose profile can be computed for a first set, e.g., 50 or so densities above that of water and below that of the maximum expected, and 50 or so densities below that of water and above the minimum expected. Also for example, the scatter dose profile can be computed for a second set, e.g., 5 or so densities above that of water and below that of the maximum expected, and 5 or so densities below that of water and above the minimum expected. To reduce the number of computations, and because scatter dose is less affected by density variations than primary dose, a lower number of scatter dose densities can be selected. Note, the 100/10 density/media selection is by way of example and should not be considered limiting.

The step or operation of parameterizing a machine-dependent dose model for unit density can include separating primary and scatter dose from a total dose equation applied to a water like medium and solving a set of equations, described previously. The step or operation of determining a machine-dependent primary dose profile can include forming a primary dose profile table for each of the electron densities in the first set of electron densities in response to received data parameters, and forming a scatter dose profile table for each of the electron densities in the second set of electron densities in response to received data parameters. According to the exemplary embodiment, the data can be retrieved from the tables using the local density of a particular point of interest or density distribution adjacent the point of interest.

The step or operation of predetermining a depth dependent representation of central axis properties of a pencil beam passing through a complex medium for each of a plurality of pencil beams can include determining for each pencil beam a depth dependent weight factor $w(d)$ for each of a plurality of depths along a central axis of the respective pencil beam. Each of the plurality of depths for each pencil beam has a density $\rho$ at each depth generally determined from, for example, the CT scan. Each depth dependent weight factor $w(d)$ can be applied to at least one function within an least two-dimensional density dependent primary dose profile associated with the depth of the respective point. Its value can be selected or otherwise determined so that when a point of interest is selected along the central axis of the respective pencil beam at the respective depth, the associated at least two-dimensional density dependent primary dose profile provides a value substantially equal to a convoluted value of central axis primary dose of the current depth when a point of interest applied to the linear combination at the current depth is on the central axis. The step or operation can also include determining a depth-dependent effective density $\rho'(d)$ for each of the plurality of depths to apply to a scatter dose profile that, when applied, provides a dose value substantially equal to a convoluted value of central axis scatter dose when a point of interest applied to the scatter dose profile at the current density at the current depth is on the central axis. The $w(d)$, $\rho'(d)$, along with $\rho_{prev}(d)$ can be stored in look-up tables associated with each of the of pencil beams.

The step or operation of determining with constant time computational complexity radiation dose for each of a plurality of points of interest in a heterogeneous medium having a complex spatial distribution of heterogeneous electron densities can include determining for each of a plurality of points of interest a local electron density value. The local electron density value can be a single value of electron density associated with the point of interest or an electron density distribution associated with the point of interest. The step or operation can also include retrieving from a look-up table or otherwise accessing predetermined off-axis properties corresponding to a homogeneous density having a value derived from the respective local electron density value associated with each point of interest in response to the respective local electron density value for each respective one of the plurality of points of interest to thereby determine radiation dose for each of the plurality of points of interest. For inverse planning, for example, where the intensity of the FSPB is being modulated, the tables can also be accessed through a combination of density and pencil beam intensity for each associated pencil beam directed through each respective one of the plurality of points of interest. The step or operation can further include displaying and at least two-dimensional but preferably a three or four dimensional map of radiation dose delivered to the patient volume to allow a user to iteratively evaluate the total dose delivered to the patient volume.

Figure 25:
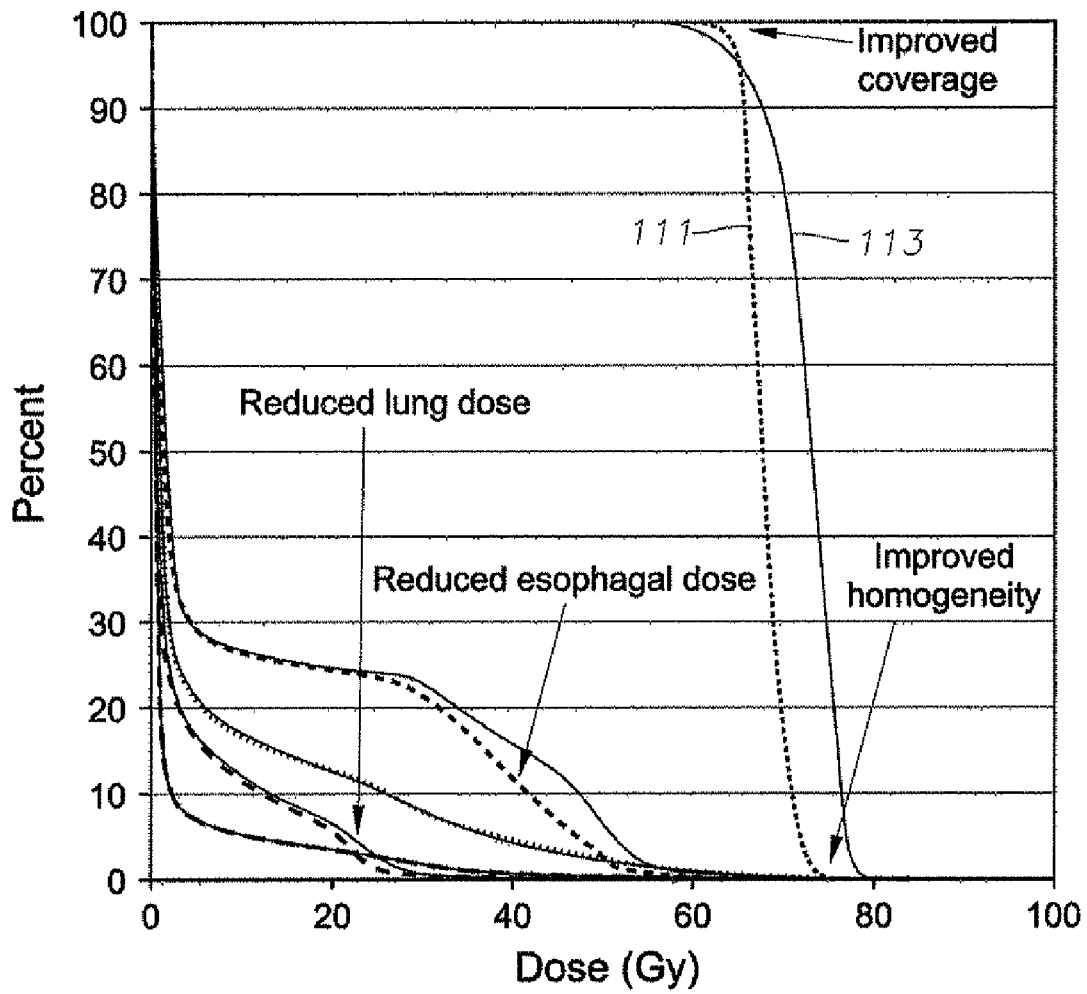
FIG. 25 is a graph illustration of a comparison of central dose volume histograms from intensity modulated radiation therapy optimization using the traditional model and the new model according to an embodiment of the present invention.

FIGS. 20A-24 illustrate the benefits of solving the problems of lateral disequilibrium, multiple dose build-up and build-down zones, and laterals heterogeneities and the agreement between the new FSPB model and Monte Carlo and its application during inverse planning as well as providing a final calculation in attaining an improved treatment plan. The new model provides nearly the accuracy of Monte Carlo, particularly in media having electron densities that very continuously, but with a constant time computational complexity, allowing for its use in performing multiple iterations of dose determinations. Further, FIG. 25 illustrates a comparison of central dose volume histograms from intensity modulated radiation therapy optimization (inverse planning) in along material using the new model vs. the traditional model, with the final dose being calculated using Monte Carlo. Referring to the target PTV curve 111, 113, for the new model and the traditional model, respectively, it can be seen that the new model enhances the ability to provide the target a higher minimum dose (improved coverage) and a lower maximum dose (improved homogeneity).

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-RWs, DVD+R/RWs, flash drives, and other newer types of memories, and transmission type media such as digital and analog communication links.

For example, such media can include the radiation treatment planning program product 37 and operating instructions related to the method steps, described above. For example, the computer readable medium can include instructions that when executed, for example, by the processor 35, allow the computer 31 to perform the operations of predetermining a delivery machine-dependent representation of radiation dose for a plurality of different electron densities selected over a preselected representative range, and predetermining for each of a plurality of pencil beams a depth-dependent representation of central axis properties of a pencil beam passing through a complex medium having a complex spatial distribution of heterogeneous electron densities. The instructions can also include those to perform the operations of determining with constant time computational complexity radiation dose for each of a plurality of points of interest in the complex medium by applying the predetermined machine-dependent and depth-dependent representations, and producing a map of radiation dose delivered to the patient volume to allow a user to iteratively evaluate the total dose of the patient volume, according to the method and operation steps described in detail above.

Embodiments of the present invention also provide a computer memory element containing, stored in signal bearing media, a database 61. The database 61 can include data in computer readable format indicating, for example, various parameters and primary and scatter dose models, depending upon which set of parameters of the model are used. For example, the data can include $N_{\rho(d)}(x,y)$ for a first set of density values, $S_\rho(x,y,d)$ for a second set of density values, and $\rho_{prev}(d))$, $w(d)$, and $\rho'(d)$ for a plurality of FSPBs, each described above. According to an embodiment of the system 30, the above parameters can be stored in the database 61 in the form of look-up tables to allow ready access.

Table 1, below, provides a glossary of commonly used terms.

TABLE 1

| Glossary: | |
| --- | --- |
| Build-down region | Upon transitioning from a depth with high density to a low density, the central axis dose smoothly builds down to the lower dose value (see FIG. 8). |
| Build-up dose region | Upon transitioning from a depth with low density to a high density, the central axis dose smoothly builds up to the lower dose value (see FIG. 8). |

TABLE 1-continued

| Glossary: | |
| --- | --- |
| Central Axis (CAX) Dose: | Dose on the central axis of a beam. |
| Complex Media: | A media for which the electron density varies arbitrarily depending upon the position in the volume. |
| Constant Time Computational Complexity: | When an algorithm has constant time computational complexity, it's calculation time does not depend on the size of the input ("O(1)" in the "big-O" notation which is a standard in computer science). |
| Clarkson Integration: | A known technique used for calculating radiation dose to a complex radiation field by adding dose contributed by a plurality of small sectors. Dose for each sector is derived from central axis dose as a function of field size. |
| Electron density | The electron density is determined by the equation $N_A(Z/A)\rho_m$, where $N_A$ is Avogadro's number, Z is the atomic number, A is the atomic weight, and $\rho_m$ is the mass density (See Task Group Report, p. 18). Such values can be derived from computed tomography (CT) scans. Typically, the continuous distribution of electron densities through-out the patient body would be determined by scanning the patient in a computed tomography machine. |
| Field size | The spatial dimensions or area of the radiation. |
| Homogeneous media: | A media having a single, uniform electron density throughout the volume. |
| Lateral Heterogeneities: | Variation in electron density across the beam front (rather than with depth). |
| Local Density | The electron density at the location of interest (rather than the density on pencil-beam central axis). |
| Longitudinal buildup coefficients | Coefficients of the model which control the change of central axis dose with depth (build-up and build-down) transitioning from one media to another (eg β and δ). |
| Off-axis profiles: | A two dimensional distribution of dose which includes an element on the central axis of the beam as well as a plurality of elements distal from the central axis. |
| Primary Dose: | The component of dose deposited by photons which are interacting in the patient for the first time as well as dose from electrons generated directly by these photons. |
| Relative Electron density (ρ): | The electron density normalized so that water has unit relative electron density. One typically expects the lung to have a relative electron density of ~0.25, while one expects bone to have a relative electron density ~1.85. Muscle and adipose tissues typically have a relative electron density ~1.0. |
| Scatter Dose: | The component of dose deposited by photons which have already interacted in patient at least once. |

Table 2 provides a plurality of references, each of which are incorporated herein by reference in their entireties.

TABLE 2

References

[1] CORVUS ® Inverse Treatment Planning, CORVUS User's Manual, North American Scientific, NOMOS Radiation Oncology Division, p. A1-A38 (2006).
[2] CORVUS ® Inverse Treatment Planning, CORVUS Beam Utilities User's Manual, North American Scientific, NOMOS Radiation Oncology Division, D1-D26 (2006).
[3] U.S. patent application 20050111621, "Planning System, Method and Apparatus for Conformal Radiation Therapy."
[4] P. S. Nizin, "Phenomenological Dose Model for Therapeutic Photon Beams: Basic Concepts and Definitions," Med. Phys. 26, p. 1893-1900 (1999).
[5] B. E. Bjärngard, P. L. Petti, "Description of the Scatter Component in Photon-Beam Data," Phys. Med. Biol. 33, p. 21-32 (1988).
[6] B. E. Bjärngard, R. L. Siddon, "A Note on Equivalent Circles, Squares, and Rectangles," Med. Phys. 9, p. 258-260 (1982).
[7] P. S. Nizin, "Electronic Equilibrium and Primary Dose in Collimated Photon Beams," Med. Phys. 20, p. 1721-11729 (1993).
[8] A. Ahnesjö, M. Saxner, A. Trepp, "A Pencil Beam Model for Photon Dose Calculation," Med. Phys. 19, p. 263-273 (1992).
[9] F. M. Khan, "The Physics of Radiation Therapy," $3^{rd}$ Ed., Lippincott, Williams &Wilkins, Philadelphia (2003).
[10] Task Group 65 Report, "Tissue InhomogeneIty Corrections for Megavoltage Photon Beam," AAPM Report 85, Medical Physics Publishing, Madison (2004).
[11] R. Jeraj, P. J. Keall, J. V. Siebers, "The Effect of Dose Calculation Accuracy on Inverse Treatment Planning," Phys. Med. Biol. 47, p. 391-407 (2002).
[12] A. O. Jones, I. J. Das, "Comparison of Inhomogeneity Correction Algorithms in Small Photon Fields," Med. Phys. 32, p. 766-776 (2005).
[13] L. Santanam, T. He, M. Yudelev, J. Burmeister, "Applicability of CORVUS Pencil Beam Model and Scatter Dose for Intensity Modulated Neutron Therapy," Phys. Med. Biol. 49, p. 3751-3766 (2004).
[14] T. Cormen, et al, "Introduction to Algorithms," The MIT Press, Cambridge Massachusetts p. 26-27, 787-791 (1997).
[15] M Romesberg, R Riker, R Hill, J Denisi, and D Spellman, "SU-DD-A1-05: Real-Time Isodose Sculpting, CDVH Manipulation, and Delivery Efficiency Control in IMRT," Med. Phys. 32, p. 1896 (2005).
[16] A. Van Esch, "Testing of the Analytical Anisotropic Algorithm for Photon Dose Calculation," Med. Phys. 33, 4130 (2006)
[17] Iwasaki, "A Method of Calculating High-Energy Photon Primary Absorbed Dose In Water Using Forward and Backward Spread Dose-Distribution Functions," Med. Phys. 12, 731 (1985).
[18] C. Hartmann, "Description and Dosimetric Verification of the PEREGRINE ® Monte Carlo Dose Calculation System for Photon Beams Incident on a Water Phantom," Med. Phys. 28, 1322 (2001)
[19] A. Ahnesjo, "Collapsed Cone Convolution of Radiant Energy for Photon Dose Calculation in Heterogeneous Media," Med. Phys. 16, 577 (1989).
[20] Siebers, "Performance of a hybrid MC dose algorithm for IMRT optimization dose evaluation," Med. Phys. 34, 2853 (2007).
[21] Bergman, "Direct Aperture Optimization for IMRT Using Monte Carlo Generated Beamlets," Med. Phys. 33, 3666 (2006).

This non-provisional application is also related to U.S. Patent Application No. 60/833,653 filed on Jul. 26, 2006, titled "System for Enhancing Intensity Modulated Radiation Therapy, Program Product, and Related Methods," also incorporated herein by reference in its entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims.

The invention claimed is:

1. A system for determining dose in heterogeneous media of varying electron density from a therapeutic high-energy radiation-beam for radiation treatment, comprising:
  a communication network;
  an image gathering device accessible to the communication network to provide an at least two-dimensional image slice of a target volume and an adjacent structure volume in a patient defining a patient volume;
  a radiation beam source to deliver radiation to the target volume according to a radiation treatment plan along a plurality of pencil beams;
  a radiation treatment planning computer in communication with the image gathering device and having memory and a processor coupled to the memory; and
  radiation treatment planning program product stored in the memory of the radiation treatment planning computer and adapted for enhanced optimization of a radiation treatment plan for delivering radiation to the target volume, the radiation treatment planning program product including instructions that when executed by the processor of the radiation treatment planning computer causes the computer to perform the operations of:
    receiving a set of photon beam data for a water medium to thereby parameterize a dose model for unit relative electron density, parameterizing a machine-dependent dose model for unit relative electron density responsive to the set of photon beam data, determining a machine-dependent primary dose profile for each of a first set of a plurality of electron densities distributed through a preselected range of electron densities responsive to the dose model for unit relative electron density, determining a machine-dependent scatter dose profile for each of a second set of a plurality of electron densities distributed through a preselected range of electron densities responsive to the dose model for unit relative electron density, determining patient specific primary dose profile parameters for each of the plurality of pencil beams to be utilized during radiation treatment responsive to the primary dose profiles, determining patient specific scatter dose profile parameters for each of the plurality of pencil beam to be utilized during radiation treatment, retrieving the patient specific primary and scatter dose profile parameters separately for each of a plurality of points of interest in a patient volume to compute dose with constant time computational complexity for each pencil-beam to each point of interest as selected a posteriori to profile parameter determination responsive to one of the following: a value of electron density associated with the respective point of interest and an electron density distribution associated with the respective point of interest, defining a local electron density value for the respective point of interest, to thereby determine total dose at each of the plurality of points of interest, and producing a map of radiation dose delivered to the patient volume to allow a user to iteratively evaluate the total dose of the patient volume.

2. A system as defined in claim 1, wherein the operations of determining machine-dependent primary dose profiles for each of the electron densities in the first set of electron densities includes performing the operations of separating a total dose model into a central axis primary and scatter dose models, and performing a two-dimensional convolution of the associated geometric kernel and radiological kernel of the respective electron density with an aperture description of a characteristic pencil beam; and wherein the operation of determining a machine-dependent scatter dose profiles for a second set of electron densities distributed through a preselected range of electron densities includes performing the operations of accessing the dose model for unit relative electron density to obtain profile data using a beam field size equal to a product of beam field size by each respective electron density.

3. A system as defined in claim 1, wherein the operation of determining patient specific primary dose profile parameters for each pencil beam to be utilized during radiation treatment includes the operations of modeling a plurality dose build-up and dose build-down regions; and wherein the operation of determining patient specific scatter dose profile parameters for each pencil beam to be utilized during radiation treatment includes determining an effective electron density.

4. A system as defined in claim 1, wherein the radiation treatment planning program product further includes instructions to perform the operations of:

storing two-dimensional primary dose profiles in separate look-up tables for each electron density in the first set of electron densities;

storing three-dimensional scatter dose profiles in separate look-up tables for each electron density in the second set of electron densities; and storing the primary and scatter dose profile parameters in separate look-up tables for each of the plurality of pencil beams.

5. A system for determining dose in a media of varying electron density from a high-energy radiation-beam for radiation treatment, comprising:

a radiation treatment planning computer having memory and a processor in communication with the memory; and radiation treatment planning program product stored in the memory of the radiation treatment planning computer and adapted to determine dose for a radiation treatment plan to deliver radiation to a complex medium defining a patient volume, the radiation treatment planning program product including instructions that when executed by the processor of the radiation treatment planning computer causes the computer to perform the operations of:

receiving measured dose data for unit relative electron density, determining machine-dependent primary dose profiles for each of a first set of a plurality of electron densities distributed through a preselected range of electron densities responsive to the measured dose data for unit relative electron density, determining machine-dependent scatter dose profiles for each of a second set of a plurality of electron densities distributed through a preselected range of electron densities responsive to the measured dose data for unit relative electron density, and using the primary and scatter dose profiles to compute dose with constant time computational complexity for each of a plurality of points of interest in the complex medium responsive to one of the following: a value of electron density associated with the respective point of interest and an electron density distribution associated with the respective point of interest, defining a local electron density value for the respective point of interest, to thereby determine total dose at each of the plurality of points of interest.

6. A system as defined in claim 5, wherein the radiation treatment planning program product further includes instructions to perform the operations of:

determining patient specific primary dose profile parameters for each of a plurality of pencil beams to be utilized during radiation treatment responsive to the primary dose profiles; and determining patient specific scatter dose profile parameters for each of the plurality of pencil beam to be utilized during radiation treatment.

7. A system as defined in claim 6, wherein the radiation treatment planning program product further includes instructions to perform the operation of retrieving the patient specific primary and scatter dose profile parameters separately for each of the plurality of points of interest in the patient volume responsive to one of the following: a value of electron density associated with the respective point of interest and an electron density distribution associated with the respective point of interest, defining the local electron density value for the respective point of interest to determine total dose at each of the plurality of points of interest, to thereby produce a three-dimensional map of radiation dose delivered to the patient volume.

8. A system as defined in claim 5, wherein the operation of determining machine-dependent primary dose profiles includes performing for each electron density in the first set of electron densities a two-dimensional radiological kernel integration convolved with geometric penumbra kernel whereby a central axis primary dose implied by the kernel is substantially equivalent to a central axis primary dose in water of a field size substantially equal to a desired field size multiplied by a ratio of electron density of the homogeneous medium to electron density of water.

9. A system as defined in claim 5, wherein the operation of determining a machine-dependent scatter dose profiles for a second set of electron densities distributed through a preselected range of electron densities includes performing for each electron density in the second set of electron densities a modified Clarkson integration whereby central axis dose in the homogeneous medium is derived from the central axis dose of water for a field size equal to the field size of the pencil beam multiplied by a ratio of an electron density of the homogeneous medium to an electron density of water.

10. A system as defined in claim 6,
wherein the operation of determining patient specific primary dose profile parameters for each pencil beam to be utilized during radiation treatment includes using a electron density-dependent kernel and combining linearly current and previous depth-dependent electron densities to determine the primary dose profile parameters around media boundaries; and
wherein the operation of determining patient specific scatter dose profile parameters for each pencil beam to be utilized during radiation treatment includes performing a modified Clarkson integration for a set of electron densities.

11. A method of determining dose in a media of varying electron density from a high-energy radiation-beam for radiation treatment, the method comprising the steps of:
predetermining a delivery machine-dependent representation of radiation dose for a plurality of different homogeneous media, each having an electron density selected over a preselected representative range;
predetermining a depth-dependent representation of central axis properties of a pencil beam passing through a complex medium having a complex spatial distribution of heterogeneous electron densities for each of a plurality of pencil beams; and
determining with constant time computational complexity, radiation dose for each of a plurality of points of interest in the complex medium, by applying the predetermined machine-dependent and depth-dependent representations.

12. A method as defined in claim 11, wherein the step of predetermining a delivery machine-dependent representation of radiation dose includes the steps of determining an at least two-dimensional primary dose profile for each of the plurality of different electron densities and an at least two-dimensional scatter dose profile for at least a representative portion of the plurality of different electron densities.

13. A method as defined in claim 11, wherein the step of predetermining a depth dependent representation of central axis properties of a pencil beam passing through a complex medium for each of a plurality of pencil beams includes the steps of:
determining a depth-dependent weighted value to form a weight for a primary dose profile for a point at a current electron density at a current depth and a weight for at least one dose profile for a corresponding at least one point at a previous electron density at a previous depth so that when the weighted values are applied to a linear combination of the dose profiles a resulting dose profile provides a value substantially equal to a computed value of central axis primary dose at the current depth when a point of interest applied to the linear combination at the current depth is on the central axis; and
determining an effective electron density to apply to a scatter dose profile that when applied provides a value substantially equal to a computed value of central axis scatter dose at the current depth when a point of interest applied to the scatter dose profile at the current electron density at the current depth is on the central axis.

14. A method as defined in claim 11, wherein the step of determining with constant time computational complexity, radiation dose for each of a plurality of points of interest in the complex medium includes the steps of:
determining for each of the plurality of points of interest at least one of the following: a value of electron density associated with the point of interest and an electron density distribution associated with the point of interest defining a local electron density value; and
accessing predetermined off-axis properties corresponding to a homogeneous electron density having a value derived from the respective local electron density value associated with each point of interest responsive to the respective local electron density value for each respective one of the plurality of points of interest and a pencil beam intensity for each associated pencil beam directed through each respective one of the plurality of points of interest to thereby determine radiation dose for each of the plurality of points of interest.

15. A method as defined in claim 11,
wherein the step of predetermining a delivery machine-dependent representation of radiation dose includes the step of determining a radiation dose profile for a plurality of media each having a different electron density, the electron densities selected over a representative range; and
wherein the step of predetermining a depth dependent representation of central axis properties of a pencil beam passing through a complex medium for each of a plurality of pencil beams includes the steps of:
determining for each of the plurality of pencil beams a depth dependent weight factor for each of a plurality of depths along a central axis of the respective pencil beam, each of the plurality of depths for each of the plurality of pencil beams having a determined electron density, each depth dependent weight factor to be applied to at least one function within an least two-dimensional electron density dependent primary dose profile associated with the depth of the respective point and having a value determined so that when a point of interest is selected along the central axis of the respective pencil beam at the respective depth, the associated at least two-dimensional electron density dependent primary dose profile provides a value substantially equal to a convoluted value of central axis primary dose of the current depth when a point of interest applied to the linear combination at the current depth is on the central axis, and
determining an effective electron density to apply to a scatter dose profile that when applied provides a value substantially equal to a convoluted value of central axis scatter dose when a point of interest applied to the scatter dose profile at the current electron density at the current depth is on the central axis.

16. A method as defined in claim 11,
wherein the step of predetermining a delivery machine-dependent representation of radiation dose includes the steps of:
receiving data parameters for a medium having properties substantially similar to that of water,
forming a primary dose profile table for each of the plurality of electron densities responsive to the data parameters, and
forming a scatter dose profile table for at least a representative portion of the plurality of electron densities;
wherein the step of predetermining a depth dependent representation of central axis properties of a pencil beam passing through a complex medium for each of a plurality of pencil beams includes the steps of:
receiving electron density parameters for a patient volume developed from a patient-specific image generating device,
determining current and previous electron density values for each of a plurality of depths along each separate one of a plurality of pencil beams,
determining a separate depth dependent weight w(d) for each of the plurality of depths, and
determining a depth-dependent effective electron density $\rho'(d)$ for each of the plurality of depths, to thereby form at least one table of off-axis dose parameters including representations of a plurality of regions of dose build-up and dose build-down; and
wherein the step of determining with constant time computational complexity radiation dose for each of a plurality of points of interest in the complex medium includes the steps of:
determining for each of a plurality of points of interest at least one of the following: a value of electron density associated with the point of interest and an electron density distribution associated with the point of interest, defining a local electron density value, and
retrieving the stored off-axis dose parameters responsive to the local electron density value for each of the plurality of points of interest.

17. A method as defined in claim 11, wherein the step of predetermining a depth dependent representation of central axis properties of a beam passing through a complex medium for each of a plurality of pencil beams includes the step of modeling a three-dimensional primary dose profile by:
linearly combining two profiles, the first profile at a current electron density and the second profile at a previous electron density to form a model of a three-dimensional primary dose profile; and
setting weighted values of each profile so that the model provides a convoluting value of the central axis primary dose when a point applied to the model at the current depth is on the central axis.

18. A method as defined in claim 11, wherein the method is applied to enable at least one of the following: inverse planning, forward plan dose calculation, and interactive dose calculation.

19. A method as defined in claim 11, wherein the high-energy radiation-beam includes one of the following: photons, electrons, neutrons, and protons.

20. A method as defined in claim 11, wherein the step of predetermining a depth dependent representation of central axis properties of a beam passing through a complex medium for each of a plurality of pencil beams includes for each of the plurality of pencil beams the step of modeling a dose profile by determining a differential change to central axis dose traveling into the complex medium along the central axis of the respective pencil beam in proportion to a product of a difference between a current central axis dose and a dose to a homogeneous medium having an electron density at a point of interest and an electron density dependent proportionality constant that depends on the electron density at the point of interest to thereby form representations of a plurality of regions of dose build-up and dose build-down.

21. A method as defined in claim 20,
wherein the step of determining a differential change to central axis dose is applied to at least one of the following: primary dose and scatter dose; and
wherein the electron density-dependent proportionality constant depends on a ratio of electron density of the medium and an associated proportionality constant applied to a medium having properties substantially similar to that of water.

22. A method of determining central axis dose in a media of varying electron density from a high-energy radiation-beam for radiation treatment, the method comprising the step of modeling a dose profile by performing the steps of:
determining a difference between a current central axis dose and a central axis dose at previous depth traveling into a complex medium along a central axis of a pencil beam in proportion to a product of a difference between the central axis dose at previous depth and an equilibrium dose to a homogeneous medium having an electron density at a point of interest, and an electron density dependent proportionality constant that depends on the electron density at the point of interest; and
determining the sum of the central axis dose at previous depth and the difference between the current central axis dose and the central axis dose at previous depth, to thereby form representations of a plurality of regions of dose build-up and dose build-down.

23. A method as defined in claim 22,
wherein the step of determining a differential change to central axis dose is applied to at least one of the following: primary dose and scatter dose; and
wherein the electron density-dependent proportionality constant depends on a ratio of electron density of the medium and an associated proportionality constant applied to a medium having properties substantially similar to that of water.

24. A method of determining an off-axis dose profile actions in heterogeneous media of varying electron density from a therapeutic high-energy radiation-beam for radiation treatment, the method comprising the steps of:
receiving a central axis primary dose;
receiving homogeneous medium off-axis primary dose profiles for a plurality of electron densities; and
determining an off-axis primary dose profile for a region of a complex medium having an electron density varying with depth along a central axis of a pencil beam by forming a combination of the homogeneous medium off-axis primary dose profiles weighted by values applied so that the center of the determined off-axis primary dose profile has primary dose equal the received central axis primary dose.

25. A method as defined in claim 24, wherein the step of determining an off-axis primary dose profile includes the step of linearly combining a two-dimensional primary dose profile for a point having a electron density value related to a current depth with a two-dimensional primary dose profile for the point having a electron density value related to that of the previous depth to form an off-axis dose profile for the complex medium.

26. A method of determining an off-axis dose profile in heterogeneous media of varying electron density from a therapeutic high-energy radiation-beam for radiation treatment, the method comprising the steps of:
receiving a central axis scatter dose;
receiving homogeneous medium off-axis scatter dose profiles for a plurality of electron densities; and
determining an off-axis scatter dose profile for a region of a complex medium having an electron density varying with depth along a central axis of a pencil beam from off-axis properties of a homogeneous medium corresponding to an effective electron density selected so that central axis scatter dose of the determined homogeneous medium off-axis scatter dose profile matches the received central axis scatter dose of the complex medium.

27. A method as defined in claim 26, wherein the step of determining an off-axis scatter dose profile includes the step of determining an effective electron density to apply to the off-axis scatter dose profile that when applied provides a value substantially equal to a convoluted value of the central axis scatter dose of the complex medium when a point of interest applied to the off-axis scatter dose profile at the current electron density at the current depth is on the central axis.

28. A method of determining dose for a pencil beam to a point of interest in a complex media having an electron density distribution varying laterally at a depth associated with the point of interest from a therapeutic high-energy radiation-beam for radiation treatment, the method comprising the steps of:
receiving a central axis dose for the pencil beam;
responsive to the received central axis dose, determining a homogeneous medium off-axis dose profile for each of a plurality of electron densities forming the electron distribution near the point of interest and at the depth associated with the point of interest, each homogeneous medium off-axis dose profile determined at a respective associated off-axis position of interest associated with a separate one of the plurality of electron densities forming the electron distribution; and
combining each of the homogeneous medium off-axis dose profiles to determine the off-axis dose profile for the pencil beam to the point of interest of the complex medium having an electron density distribution varying laterally at the depth associated with the point of interest responsive to the homogeneous medium profiles.

29. A method of determining dose for a pencil beam to a point of interest in a complex media having an electron density distribution varying laterally at a depth associated with the point of interest from a therapeutic high-energy radiation-beam for radiation treatment, the method comprising the steps of:
receiving a central axis dose for the pencil beam;
responsive to the received central axis dose, determining a homogeneous medium off-axis dose nrofile for each of a plurality of electron densities forming the electron distribution near the point of interest and at the depth associated with the point of interest, each homogeneous medium off-axis dose profile determined at a respective associated off-axis position of interest associated with a separate one of the plurality of electron densities forming the electron distribution; and
selecting one of the plurality of homogeneous medium off-axis dose profiles for a single electron density value to determine the off-axis dose profile for the pencil beam to the point of interest of the complex medium having an electron density distribution varying laterally at the depth associated with the point of interest.

30. A method of determining dose in heterogeneous media of varying electron density from a therapeutic high-energy radiation-beam for radiation treatment, the method comprising the step of:
determining for a preselected size pencil beam, a central axis primary dose in a homogeneous medium of arbitrary electron density from a central axis primary dose model for water equivalent medium of an equivalent effective field size by rescaling a dose normalization factor and a linear attenuation and longitudinal buildup coefficients as a function of the arbitrary electron density.

31. A method as defined in claim 30, wherein the step of determining central axis primary dose includes the step of modifying a two-dimensional radiological kernel representing electron transport so that a central axis dose implied by the kernel is substantially equivalent to a central axis dose in water of a pencil beam field size substantially equal to a desired field size multiplied by a ratio of electron density of the homogeneous medium to electron density of water by employing a representation of a dose normalization factor expressed as a linear combination of exponential functions that model lateral electron transport whose longitudinal buildup coefficients scale linearly with electron density.

32. A method of determining dose in heterogeneous media of varying electron density from a therapeutic high-energy radiation-beam for radiation treatment, the method comprising the steps of:
receiving a central axis scatter dose model representing central axis scatter dose as a function of field size and depth for water equivalent medium;
determining a central axis scatter dose model representing central axis scatter dose as a function of field size and depth for a homogeneous medium of arbitrary electron density using an equivalent effective field size responsive to the received scatter dose model; and
determining at least one scatter volume for a homogeneous medium of arbitrary electron density by performing a modified Clarkson integration utilizing the determined central axis scatter dose model of the homogeneous medium of arbitrary electron density in the integration to derive the scatter volume.

33. A method as defined in claim 32,
wherein the equivalent field size is equal to the field size in the homogeneous medium of arbitrary electron density multiplied by a ratio of an electron density of the homogeneous medium to an electron density of water; and
wherein the step of determining central axis scatter dose model for the water equivalent medium includes the step of applying a linear fit of a measured total central axis dose as a function of a distance variable, to separate the central axis scatter dose from a central axis primary dose.

34. A computer readable medium that is readable by a computer, the computer readable medium comprising a set of instructions that, when executed by the computer, cause the computer to perform the following operations:
predetermining a delivery machine-dependent representation of radiation dose for a plurality of different electron densities selected over a preselected representative range;

predetermining for each of a plurality of pencil beams, a depth-dependent representation of central axis properties of a pencil beam passing through a complex medium having a complex spatial distribution of heterogeneous electron densities; and determining with constant time computational complexity, radiation dose for each of a plurality of points of interest in the complex medium by applying the predetermined machine-dependent and depth-dependent representations.

35. A computer readable medium as defined in claim 34, wherein the operation of predetermining a delivery machine-dependent representation of radiation dose includes the operations of determining an at least two-dimensional primary dose profile for each of the plurality of different electron densities and an at least two-dimensional scatter dose profile for at least a representative portion of the plurality of different electron densities.

36. A computer readable medium as defined in claim 34, wherein the operation of predetermining for each of a plurality of pencil beams a depth dependent representation of central axis properties of a pencil beam passing through a complex medium includes the operations of:

determining a depth-dependent weighted value to form a weight for a primary dose profile for a point at a current electron density at a current depth and a weight for at least one dose profile for a corresponding at least one point at a previous electron density at a previous depth so that when the weighted values are applied to a linear combination of the dose profiles a resulting dose profile provides a value substantially equal to a convoluted value of central axis primary dose at the current depth when a point of interest applied to the linear combination at the current depth is on the central axis; and determining an effective electron density to apply to a scatter dose profile that when applied provides a value substantially equal to a convoluted value of central axis scatter dose at the current depth when a point of interest applied to the scatter dose profile at the current electron density at the current depth is on the central axis.

37. A computer readable medium as defined in claim 34, wherein the operation of determining with constant time computational complexity, radiation dose for each of a plurality of points of interest in a complex medium includes the operations of:

determining for each of a plurality of points of interest at least one of the following: a value of electron density associated with the point of interest and an electron density distribution associated with the point of interest defining a local electron density value; and accessing predetermined off-axis properties corresponding to a homogeneous electron density having a value derived from the respective local electron density value associated with each point of interest responsive to the respective local electron density value for each respective one of the plurality of points of interest and a pencil beam intensity for each associated pencil beam directed through each respective one of the plurality of points of interest to thereby determine radiation dose for each of the plurality of points of interest.

38. A computer readable medium as defined in claim 34, wherein the operation of predetermining a delivery machine-dependent representation of radiation dose includes the operation of determining a radiation dose profile for a plurality of media each having a different electron density, the electron densities selected over a representative range; and wherein the operation of predetermining for each of a plurality of pencil beams, a depth dependent representation of central axis properties of a pencil beam passing through a complex medium for each of a plurality of pencil beams includes the operations of:

determining for each of the plurality of pencil beams a depth dependent weight factor for each of a plurality of depths along a central axis of the respective pencil beam, each of the plurality of depths for each of the plurality of pencil beams having a determined electron density, each depth dependent weight factor to be applied to at least one function within an least two-dimensional electron density dependent primary dose profile associated with the depth of the respective point and having a value determined so that when a point of interest is selected along the central axis of the respective pencil beam at the respective depth, the associated at least two-dimensional electron density dependent primary dose profile provides a value substantially equal to a convoluted value of central axis primary dose of the current depth when a point of interest applied to the linear combination at the current depth is on the central axis, and determining an effective electron density to apply to a scatter dose profile that when applied provides a value substantially equal to a convoluted value of central axis scatter dose when a point of interest applied to the scatter dose profile at the current electron density at the current depth is on the central axis.

39. A computer readable medium as defined in claim 34, wherein the operation of predetermining a delivery machine-dependent representation of radiation dose includes the operations of:

receiving data parameters for a medium having properties substantially similar to that of water, forming a primary dose profile table for each of the plurality of electron densities responsive to the data parameters, and forming a scatter dose profile table for at least a representative portion of the plurality of electron densities;

wherein the operation of predetermining for each of a plurality of pencil beams, a depth dependent representation of central axis properties of a pencil beam passing through a complex medium includes the operations of:

receiving electron density parameters for a patient volume developed from a patient-specific image generating device, determining current and previous electron density values for each of a plurality of depths along each separate one of a plurality of pencil beams, determining a separate depth dependent weight w(d) for each of the plurality of depths, and determining a depth-dependent effective electron density $\rho'(d)$ for each of the plurality of depths, to thereby form at least one table of off-axis dose parameters including representations of a plurality of regions of dose build-up and dose build-down; and wherein the operation of determining with constant time computational complexity, radiation dose for each of a plurality of points of interest in the complex medium includes the operations of:

determining for each of a plurality of points of interest at least one of the following: a value of electron density associated with the point of interest and an electron density distribution associated with the point of interest, defining a local electron density value, and retrieving the stored off-axis dose parameters responsive to the local electron density value for each of the plurality of points of interest.

40. A computer readable medium as defined in claim 34, wherein the operation of predetermining for each of a plurality of pencil beams, a depth dependent representation of central axis properties of a beam passing through a complex medium includes the operation of modeling a three-dimensional primary dose profile by:
linearly combining two dose profiles, the first dose profile at a current electron density and the second dose profile at a previous electron density to form a model of a three-dimensional primary dose profile; and
setting weighted values of each dose profile so that the model provides a convoluting value of the central axis primary dose when a point applied to the model at the current depth is on the central axis.

41. A computer readable medium as defined in claim 34, wherein the operation of predetermining for each of a plurality of pencil beams, a depth dependent representation of central axis properties of a beam passing through a complex medium includes for each of the plurality of pencil beams the operation of modeling a dose profile by determining a differential change to central axis dose traveling into the complex medium along the central axis of the respective pencil beam in proportion to a product of a difference between a current central axis dose and a dose to a homogeneous medium having an electron density at a point of interest and a electron density dependent proportionality constant that depends on the electron density at the point of interest to thereby form representations of a plurality of regions of dose build-up and dose build-down.

42. A computer readable medium as defined in claim 41,
wherein the operation of determining a differential change to central axis dose is applied to at least one of the following: primary dose and scatter dose; and
wherein the electron density-dependent proportionality constant depends on a ratio of electron density of the medium and an associated proportionality constant applied to a medium having properties substantially similar to that of water.

43. A computer readable medium as defined in claim 34, wherein the operation of predetermining for each of a plurality of pencil beams, a depth dependent representation of central axis properties of a beam passing through a complex medium for each of a plurality of pencil beams includes for each of the plurality of pencil beams the operations of:
receiving a central axis primary dose;
receiving homogeneous medium off-axis primary dose profiles for a plurality of electron densities; and
determining an off-axis primary dose profile for a region of a complex medium having an electron density varying with depth along a central axis of a pencil beam by forming a linear combination of the homogeneous medium off-axis primary dose profiles weighted by values applied so that the center of the determined off-axis primary dose profile has primary dose substantially equal to the received central axis primary dose.

44. A computer readable medium as defined in claim 43, wherein the operation of determining an off-axis primary dose profile includes the operation of linearly combining a two-dimensional primary dose profile for a point of interest having a electron density value related to a current depth with a two-dimensional primary dose profile for the point of interest having a electron density value related to that of the previous depth to form an off-axis dose profile for the complex medium.

45. A computer readable medium as defined in claim 34, wherein the operation of predetermining for each of a plurality of pencil beams, a depth dependent representation of central axis properties of a beam passing through a complex medium for each of a plurality of pencil beams includes for each of the plurality of pencil beams the operations of:
receiving a central axis scatter dose;
receiving homogeneous medium off-axis scatter dose profiles for a plurality of electron densities; and
determining an off-axis scatter dose profile for a region of a complex medium having an electron density varying with depth along a central axis of a pencil beam from off axis properties of a homogeneous medium having an effective electron density selected so that central axis scatter dose of the determined homogeneous medium off-axis profile substantially matches the received central axis scatter dose of the complex medium.

46. A computer readable medium as defined in claim 45, wherein the operation of determining an off-axis scatter dose profile includes the operation of determining an effective electron density to apply to the off-axis scatter dose profile that when applied provides a value substantially equal to a convoluted value of the central axis scatter dose for a complex medium when a point of interest applied to the off-axis scatter dose profile at the current electron density at the current depth is on the central axis.

47. A computer readable medium that is readable by a computer, the computer readable medium comprising a set of instructions that, when executed by the computer, cause the computer to perform the operations of:
receiving a central axis dose for a pencil beam at a depth associated with a point of interest of a complex medium having an electron distribution varying laterally;
receiving a homogeneous medium off-axis dose profile for each of a plurality of electron densities;
receiving the electron density distribution near the point of interest; and
responsive to the electron density distribution near the point of interest, combining each of the homogeneous medium off-axis dose profiles and the central axis dose to determine an off-axis dose profile for the pencil beam to the point of interest of the complex medium having an electron density distribution varying laterally at the depth of interest associated with the point of interest.

48. A computer readable medium as defined in claim 47, wherein the instructions further include those to perform the operation of determining central axis primary dose for a pencil beam having a field size in a homogeneous medium from a central axis primary dose model for water equivalent medium of an equivalent effective field size.

49. A computer readable medium as defined in claim 48, wherein the operation of determining central axis primary dose includes the operation of modifying a two-dimensional radiological kernel representing electron transport so that a central axis dose implied by the kernel is substantially equivalent to a central axis dose in water of a pencil beam field size substantially equal to a desired field size multiplied by a ratio of electron density of the homogeneous medium to electron density of water.

50. A computer readable medium as defined in claim 47, wherein the instructions further include those to perform the operation of determining central axis scatter dose for a pencil beam having a field size in a homogeneous medium from a central axis scatter dose model for water equivalent medium of an equivalent effective field size.

51. A computer readable medium as defined in claim 47, wherein the operation of receiving a homogeneous medium off-axis dose profile includes the operation of performing a modified Clarkson integration whereby the homogeneous medium off-axis dose profile is derived from an off-axis dose profile of water for a field size equal to the field size of the pencil beam multiplied by a ratio of an electron density of the homogeneous medium to an electron density of water.

52. A computer readable medium that is readable by a computer, the computer readable medium comprising a set of instructions that, when executed by the computer, cause the computer to perform the operations of:
receiving a central axis dose for a pencil beam at a depth associated with a point of interest of a complex medium having an electron distribution varying laterally;
receiving a homoaeneous medium off-axis dose profile for each of a plurality of electron densities;
receiving an electron density at the point of interest; and
responsive to the electron density at the point of interest, determining an off-axis dose profile for the pencil beam to the point of interest of the complex medium having an electron density distribution varying laterally at the depth associated with the point of interest, the operation of determining the off-axis dose profile including the operation of selecting one of the plurality of homogeneous medium off-axis dose profiles for a single electron density value.

53. A computer readable medium as defined in claim 52, wherein the instructions further include those to perform the operation of determining central axis primary dose for a pencil beam having a field size in a homogeneous medium from a central axis primary dose model for water equivalent medium of an equivalent effective field size.

54. A computer readable medium as defined in claim 53, wherein the operation of determining central axis primary dose includes the operation of modifying a two-dimensional radiological kernel representing electron transport so that a central axis dose implied by the kernel is substantially equivalent to a central axis dose in water of a pencil beam field size substantially equal to a desired field size multiplied by a ratio of electron density of the homogeneous medium to electron density of water.

55. A computer readable medium as defined in claim 52, wherein the instructions further include those to perform the operation of determining central axis scatter dose for a pencil beam having a field size in a homogeneous medium from a central axis scatter dose model for water equivalent medium of an equivalent effective field size.

56. A computer readable medium as defined in claim 52, wherein the operation of receiving a homogeneous medium off-axis dose profile includes the operation of performing a modified Clarkson integration whereby the homogeneous medium off-axis dose profile is derived from an off-axis dose profile of water for a field size equal to the field size of the pencil beam multiplied by a ratio of an electron density of the homogeneous medium to an electron density of water.

* * * * *